United States Patent
Wood et al.

(10) Patent No.: US 9,833,223 B2
(45) Date of Patent: Dec. 5, 2017

(54) CAPACITOR POWERED BATTERY REPLACEMENT DEVICE

(71) Applicant: Welch Allyn, Inc., Skaneateles Falls, NY (US)

(72) Inventors: Robert J. Wood, Syracuse, NY (US); Jon R. Salvati, Skaneateles, NY (US); Michael Curry, Syracuse, NY (US); Michael T. McMahon, Syracuse, NY (US); Steven R. Slawson, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 14/838,072

(22) Filed: Aug. 27, 2015

(65) Prior Publication Data

US 2016/0051238 A1 Feb. 25, 2016

Related U.S. Application Data

(62) Division of application No. 13/650,488, filed on Oct. 12, 2012, now Pat. No. 9,153,994.

(Continued)

(51) Int. Cl.
*H02J 7/00* (2006.01)
*H02J 7/14* (2006.01)
(Continued)

(52) U.S. Cl.
CPC .............. *A61B 17/00* (2013.01); *A61B 90/00* (2016.02); *H01G 9/004* (2013.01); *H02J 7/0008* (2013.01);
(Continued)

(58) Field of Classification Search
USPC ........ 320/128, 101, 110, 111, 135, 136, 137, 320/145, 162, 107, 112, 113, 115, 166;
(Continued)

(56) References Cited

U.S. PATENT DOCUMENTS

| | | |
|---|---|---|
| 4,442,382 A | 4/1984 | Fleck |
| 4,609,861 A | 9/1986 | Inaniwa et al. |

(Continued)

FOREIGN PATENT DOCUMENTS

| | | |
|---|---|---|
| EP | 2 090 256 A2 | 8/2009 |
| JP | 2008-67323 | 3/2008 |

(Continued)

OTHER PUBLICATIONS

Dirjish, M., "Ultracapacitors Branch Out Into Wider Markets," Electronic Design, Copyright 2010 Penton Media Inc., Nov. 17, 2008, accessed May 4, 2011 via electronicdesign.com/.../ ultracapacitor . . . , 3 pages.

(Continued)

*Primary Examiner* — Alexis Pacheco
(74) *Attorney, Agent, or Firm* — Merchant & Gould P.C.

(57) ABSTRACT

A handheld device includes an electronic instrument and a capacitive power supply for storing and delivering power to the electronic instrument. The capacitive power supply includes at least one capacitor, and an electronic circuit operable to boost a voltage from the capacitor to a higher voltage for use by the electronic instrument. The capacitive power supply can be rapidly recharged. Some configurations include an accelerometer which permits the handheld device to detect movement and perform various operations responsive to detected movement. A dual charging station is also disclosed.

5 Claims, 25 Drawing Sheets

Related U.S. Application Data

(60) Provisional application No. 61/547,400, filed on Oct. 14, 2011.

(51) Int. Cl.

| | | |
|---|---|---|
| *A61B 17/00* | (2006.01) | |
| *H02J 7/02* | (2016.01) | |
| *H01G 9/004* | (2006.01) | |
| *A61B 90/00* | (2016.01) | |
| *A61B 18/18* | (2006.01) | |
| *H01M 10/42* | (2006.01) | |
| *H02J 7/34* | (2006.01) | |
| *A61B 1/227* | (2006.01) | |
| *A61B 19/00* | (2006.01) | |

(52) U.S. Cl.
CPC .......... *H02J 7/0027* (2013.01); *H02J 7/0042* (2013.01); *H02J 7/0044* (2013.01); *H02J 7/0052* (2013.01); *H02J 7/0065* (2013.01); *H02J 7/02* (2013.01); *A61B 1/227* (2013.01); *A61B 18/18* (2013.01); *A61B 2017/00734* (2013.01); *A61B 2019/48* (2013.01); *A61B 2560/0214* (2013.01); *A61M 2205/8237* (2013.01); *H01M 10/42* (2013.01); *H02J 7/345* (2013.01); *H02J 2007/0067* (2013.01)

(58) Field of Classification Search
USPC ........................................................ 324/426
See application file for complete search history.

(56) References Cited

U.S. PATENT DOCUMENTS

| | | | |
|---|---|---|---|
| 5,277,993 A * | 1/1994 | Landers .............. | H01M 2/1055 |
| | | | 429/10 |
| 5,717,311 A | 2/1998 | Im et al. | |
| 6,020,719 A * | 2/2000 | Nishigaki .............. | H02J 7/345 |
| | | | 320/128 |
| 6,074,778 A * | 6/2000 | Stagakis ................. | F21L 7/00 |
| | | | 362/202 |
| 6,094,033 A | 7/2000 | Ding et al. | |
| 6,501,386 B2 | 12/2002 | Lehrman et al. | |
| 6,611,110 B1 | 8/2003 | Fregoso | |
| 6,700,352 B1 | 3/2004 | Elliott et al. | |
| 6,704,699 B2 | 3/2004 | Nir | |
| 7,323,849 B1 | 1/2008 | Robinett et al. | |
| 7,394,385 B2 | 7/2008 | Franco et al. | |
| 7,469,155 B2 | 12/2008 | Chu | |
| 8,250,921 B2 | 8/2012 | Nasiri et al. | |
| 8,408,951 B1 * | 4/2013 | Chartrand ................ | H01R 4/28 |
| | | | 362/204 |
| 2001/0035735 A1 * | 11/2001 | Fukuoka .............. | G06F 1/1613 |
| | | | 320/112 |
| 2003/0080712 A1 | 5/2003 | Tamura et al. | |
| 2003/0102845 A1 | 6/2003 | Aker et al. | |
| 2004/0251880 A1 | 12/2004 | O'Brien | |
| 2004/0263129 A1 | 12/2004 | Thrap | |
| 2005/0038388 A1 | 2/2005 | Hommann | |
| 2005/0212755 A1 | 9/2005 | Marvit | |
| 2006/0092674 A1 | 5/2006 | Belton et al. | |
| 2007/0186429 A1 | 8/2007 | Bonnet et al. | |
| 2008/0018308 A1 | 1/2008 | Daboussi | |
| 2008/0058783 A1 | 3/2008 | Altshuler et al. | |
| 2008/0111423 A1 | 5/2008 | Baker et al. | |
| 2008/0129219 A1 | 6/2008 | Smith et al. | |
| 2008/0208006 A1 | 8/2008 | Farr | |
| 2008/0258674 A1 | 10/2008 | Hui et al. | |
| 2008/0259274 A1 | 10/2008 | Chinnock | |
| 2008/0272656 A1 | 11/2008 | Mason | |
| 2009/0007661 A1 | 1/2009 | Nasiri et al. | |
| 2009/0015216 A1 | 1/2009 | Seberger et al. | |
| 2009/0096430 A1 | 4/2009 | Van Der Linde et al. | |
| 2009/0174364 A1 | 7/2009 | Onishi et al. | |
| 2009/0179613 A1 | 7/2009 | Masho | |
| 2009/0209990 A1 | 8/2009 | Yates et al. | |
| 2010/0007307 A1 | 1/2010 | Baarman et al. | |
| 2010/0094220 A1 | 4/2010 | Mandro | |
| 2010/0137779 A1 | 6/2010 | Seitz | |
| 2010/0144436 A1 | 6/2010 | Marks et al. | |
| 2010/0157638 A1 | 6/2010 | Naiknaware et al. | |
| 2010/0182075 A1 | 7/2010 | Yang et al. | |
| 2010/0225283 A1 | 9/2010 | Hsia et al. | |
| 2010/0268351 A1 | 10/2010 | van der Merwe et al. | |
| 2012/0280576 A1 | 11/2012 | Wood | |
| 2012/0280664 A1 | 11/2012 | Wood | |
| 2014/0191726 A1 * | 7/2014 | Long .................... | A47K 5/1217 |
| | | | 320/128 |

FOREIGN PATENT DOCUMENTS

| | | |
|---|---|---|
| WO | WO 2006/060391 A2 | 6/2006 |
| WO | WO 2008/093170 A2 | 8/2008 |
| WO | WO 2010/029519 A2 | 3/2010 |
| WO | WO 2010/062521 A1 | 6/2010 |
| WO | WO 2012178045 A2 * 12/2012 ........... A47K 5/1217 |

OTHER PUBLICATIONS

International Search Report and Written Opinion in PCT/US2012/035764 mailed Oct. 12, 2012, 10 pages.

Isaacson, M. et al., "Advanced Lithium Ion Battery Charger," Lockheed Martin Missiles & Space, P.O. Box 3504, Sunnyvale, CA 94089-3504, Copyright 2000, pp. 193-198.

Li, P. et al., "A Wireless Power Interface for Rechargeable Battery Operated Medical Implants," IEEE Transactions on Circuits and Systems II: Express Briefs, vol. 54, No. 10, Oct. 2007, pp. 912-916.

Park, C. et al., TurboCap A Batteryless, Supercapacitor-based Power Supply for Mini-FDPM; The University of California, Irvine, CA 92697-2625 USA and National Tsing Hua University, Hsinchu, Taiwan, 8 pages.

Simjee, F. et al., "Efficient Charging of Supercapacitors for Extended Lifetime of Wireless Sensor Nodes," IEEE Transactions on Power Electronics, vol. 23, No. 3, May 2008, pp. 1526-1536.

* cited by examiner

CAPACITOR POWERED BATTERY REPLACEMENT DEVICE

CROSS REFERENCE TO RELATED APPLICATIONS

This application is a divisional application of U.S. Ser. No. 13/650,488, now U.S. Pat. No. 9,153,994, titled MOTION SENSITIVE AND CAPACITOR POWERED HANDHELD DEVICE, filed on Oct. 12, 2012, issued on Oct. 6, 2015, which claims priority to U.S. Ser. No. 61/547,400, titled CAPACITIVE POWER SUPPLY VARIABLE CONTROL AND ACCESSORIES FOR HANDHELD DEVICE, filed on Oct. 14, 2011, the disclosures of which are incorporated by reference herein in their entireties.

BACKGROUND

Healthcare providers, such as doctors and nurses, frequently use handheld devices when providing healthcare. Many of these handheld devices include electrical devices that must be powered by electricity. One example of such a handheld device is an otoscope, which includes a light to illuminate a patient's ear canal during an examination. It is sometimes desirable to adjust the electrical device, such as to increase or decrease the brightness of the light.

Some handheld instruments include a power cable that can be plugged into a wall receptacle to deliver power to the handheld device. The power cable limits the use of the handheld instrument to locations near a wall receptacle. The power cable is also inconvenient because it can inhibit free movement of the handheld device.

Batteries are sometimes used in handheld devices to overcome the drawbacks of power cables. While batteries do allow the healthcare provider to freely move the device independent of a wall receptacle, batteries have their own limitations. Batteries must be periodically recharged or replaced. Batteries are also slow to recharge, and so the handheld device may be out of service for some time. In addition, batteries have a limited life, and can be harmful to the environment if not disposed of or recycled properly.

SUMMARY

In general terms, this disclosure is directed to a motion sensitive and capacitor powered device. In one possible configuration and by non-limiting example, the device is a handheld medical device.

One aspect is a handheld medical device comprising: an electronic device; a power source; an accelerometer operable to detect movement and orientation of the handheld medical device; and a processing device communicatively coupled to the accelerometer and configured to automatically adjust an ON/OFF state of the electronic device based at least in part on (i) a detected movement of the medical device, and (ii) a detected orientation of the medical device at a time of the detected movement.

Another aspect is a battery replacement device comprising: a packaging including at least a positive terminal and a negative terminal, the packing having a size and shape of at least one battery; at least one capacitor disposed in the packaging; and a mimic circuit electrically coupled to receive power from the capacitor and deliver the power to at least one of the positive and negative terminals, wherein the mimic circuit changes an output characteristic of the capacitor into an output characteristic of the battery.

A further aspect is A dual charging station comprising: a base including first and second connectors and at least one electrical conductor electrically connecting the first connector with the second connector; a master station having a power cord adapted to receive mains power from a wall receptacle, to connect with the first connector, and to supply at least some of the mains power to the electrical conductor at the first connector; and a slave station adapted to connect with the second connector and receive the at least some of the mains power from the electrical conductor at the second connector.

DETAILED DESCRIPTION

Figure 1:
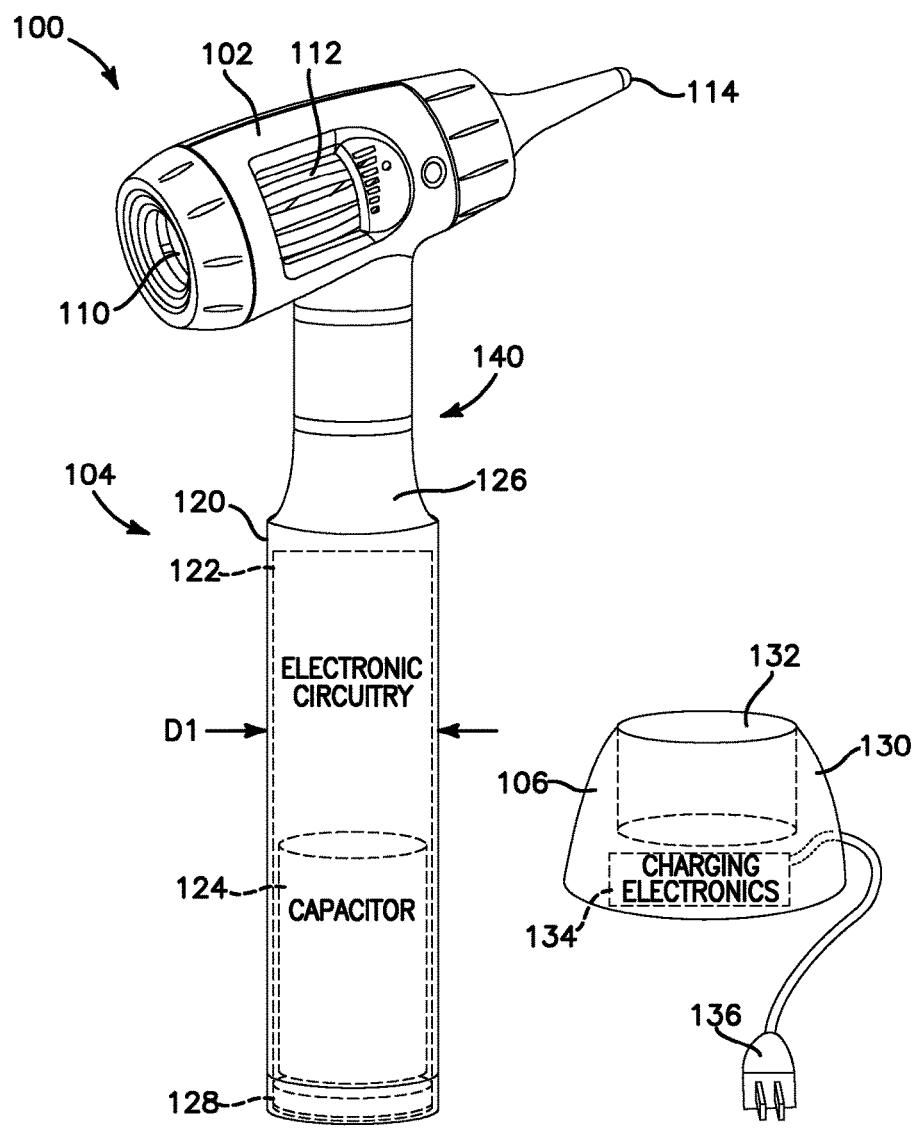
FIG. 1 is a schematic perspective view of an example handheld device.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is schematic perspective view of an example handheld device 100. In this example, the handheld device 100 includes an instrument 102 and a power handle 104. Some embodiments further include a charging station 106 for recharging the handheld device 100.

An example of instrument 102 is an otoscope, which includes an adjustable optics assembly 110, an adjustment control 112, and a light source 114. An otoscope can be used by a healthcare provider during a patient encounter to view inside a patient's ear canal. To do so, the healthcare provider inserts the end of the otoscope into the ear canal, where it is illuminated by the light source 114. The healthcare provider then looks through the optics assembly 110 and adjusts the focus, if necessary, using the adjustment control 112. As discussed below, the light source is powered by the power handle 104. Power is transferred through conductors within the instrument.

A wide variety of instruments 102 can be used in other embodiments. In some embodiments, the instrument 102 is a medical examination instrument, such as an otoscope, an ophthalmoscope, a thermometer, a sphygmomanometer, a skin surface microscope, a unidirectional occluder, an examination light, an electronic stethoscope, a tympanometric instrument, an audiometer, or a variety of other medical examination instruments. In other embodiments, the instrument 102 is a therapeutic device, such as a surgical instrument, a drug delivery or measurement instrument, or other therapeutic devices. Although exemplary embodiments are described as handheld medical devices, other embodiments are possible, such as non-handheld devices, or non-medical devices.

The power handle 104 forms a handle for the handheld device 100, and is sized to be held in the hand of the healthcare provider. In this example, the power handle 104 includes a housing 120 and electronic circuitry 122 within the housing 120. The electronic circuitry 122 includes, for example, a power source 124. In some embodiments, the power source 124 is one or more capacitors, as described in more detail herein. In some embodiments, the electronic circuitry modifies the power curve to mimic a power curve of one or more batteries. In some embodiments, the power source 124 includes one or more batteries, capacitors, power cords, power input ports, or other power sources or combinations of these or other power sources. In some embodiments, the power handle 104 further includes a variable control 126, and charging circuitry 128.

The housing 120 is, in some embodiments, sized and configured to be held by a hand of a healthcare provider. The housing 120 is typically formed of materials such as metal or plastic, and forms a protective enclosure for the electronic circuitry 122 contained within the housing 120. In some embodiments the housing 120 includes a variable control 126 built into the housing, which may be include or be formed of an insulating material, such as plastic, as discussed herein.

In some embodiments, the housing 120 has a cross-sectional dimension D1 sized to fit within a hand of a healthcare provider. In one example, the dimension D1 is in a range from about 0.5 inches to about 4 inches. In another example, the dimension D1 is in a range from about 0.5 inches to about 3 inches. In yet another example, the dimension D1 is about one inch. In some embodiments, dimension D1 is less than about 4 inches, 3 inches, or 2 inches. In some embodiments, at least a portion of the housing has a cylindrical shape, in which case the dimension D1 is the diameter of the housing.

In some embodiments, the housing 120 of the power handle 104 is sealed. Because some embodiments do not include batteries or other components that need to be removed and replaced during the life of the power handle 104, such embodiments do not require any doors or other openings, other than at the interface 140. Further, the interface 140 can also be permanently connected and sealed in some embodiments. A sealed housing 120 reduces the chance of water or other liquid or particle intrusion into the interior of housing 120. A sealed housing 120 is also easier to clean and sanitize.

As discussed herein, some embodiments include a variable control 126 that is enclosed within housing 120. This also prevents liquid or particle intrusion into the housing at the location of the variable control 126, improving the durability of the power handle 104. Similarly, some embodiments are powered with a rechargeable power source that does not need to be replaced during the life of the power handle 104. As a result, the power source can also be sealed within the housing 120 and does not require any doors or other openings, other than at the interface 140. A sealed housing 120 reduces the chance of water or other liquid or particle intrusion into the interior of housing 120. A sealed housing 120 is also easier to clean and sanitize.

The electronic circuitry 122 is a capacitive power supply that includes at least one capacitor that stores electrical energy. In some embodiments, the at least one capacitor forms the primary energy storage device of the handheld medical device.

In some embodiments, the power source 124 is a super capacitor (sometimes alternatively referred to as an ultra capacitor or a pseudo capacitor), which can store a large amount of electrical energy. In some embodiments, the capacitor includes a high capacitance, a high energy density, and/or a high power density. In some embodiments, the super capacitor has a capacitance of greater than about 100 F. Some embodiments have a power density of greater than 1,000 W/kg. Some embodiments have an energy density in a range from about 1 Wh/kg to about 10 Wh/kg. In some embodiments, the power source 124 is one or more electric double layer capacitors (EDLC).

In some embodiments, the power source 124 is an electrochemical capacitor that has a high energy density when compared to common capacitors, typically on the order of thousands of times greater than a high capacity electrolytic capacitor. For example, a typical D-cell sized electrolytic capacitor may have a capacitance in the range of tens of milli-Farads. The same size electric double-layer capacitor may have a capacitance of several farads, an improvement of about two or three orders of magnitude in capacitance, but may have a lower working voltage.

One example of a super capacitor is the pseudo electrochemical double layer capacitor distributed by Ioxus, Inc. of Oneonta, N.Y. These include the 220 F. model (Part No. RHE2R3227SR) having a power density of about 2.65 kW/kg and an energy density of about 6.47 Wh/kg, the 800 F. model (Part No. RHE2R3807SR) having a power density of about 1.82 kW/kg and an energy density of about 6.46 Wh/kg, and the 1000 F. model (Part No. RHE2R3108SR) having a power density of about 1.57 kW/kg and an energy density of about 6.12 Wh/kg. Two or more capacitors are combined to achieve the desired characteristics, in some embodiments.

In some embodiments, the at least one capacitor 124 stores a voltage equal to the maximum rated voltage of two cells in series. As one example, the maximum rated voltage of two cells in series is 4.6 v. Other embodiments utilize other voltages.

A capacitor's voltage decays rapidly over time. As a result, the electronic circuitry 122 includes circuitry in some embodiments that boosts the voltage to a desired level. Examples of the electronic circuitry 122 are described in more detail with reference to FIGS. 2-5. Alternatively, in some embodiments the power source 124 itself includes electronics that modify the capacitor power output curve to mimic a power curve of a battery or other power source, permitting the power source 124 to be utilized in devices that are designed to be powered by batteries. In some embodiments, the power source 124 is packaged in a form factor matching or similar to that of one or more batteries.

In another possible embodiment, the power source 124 is one or more batteries, such as alkaline or rechargeable batteries, that store electrical energy for powering the instrument 102, as well as the electronic circuitry 122. In some embodiments the power source 124 is not contained within the housing 120. For example, a wall receptacle is used as a power source in some embodiments, which delivers power through a power cord plugged into or extending from the housing 120. Other power sources are used in other embodiments.

A variable control 126 is provided in some embodiments to permit adjustment of the amount of power delivered from the power handle 104 to the instrument 102. One possible example of the variable control 126 is a rheostat control (also known as a potentiometer or variable resistor) that can be operated by the healthcare provider to adjust the amount of power delivered to the instrument 102, such as to increase or decrease the intensity of the light source 114.

Another possible example of the variable control 126 is a capacitive sensing variable control, as described herein.

Some embodiments do not include a variable control, but rather include an on/off control. In yet another embodiment, an on/off control or variable control is part of the instrument 102, rather than being a part of the handle 104.

The charging circuitry 128 is included in some embodiments to receive power from the charging station 106 and to deliver the power to the capacitor 124. The charging circuitry can include, for example, a coil for receiving power through magnetic fields generated by a corresponding coil of the charging station 106. The coils are placed into close proximity to one another such that inductive coupling occurs between the coils.

In another embodiment, a direct electrical connection is made between electrical contacts accessible through the housing 120 (such as through a plug or port) and the charging station 106 for providing power to the power handle.

Additional charging circuitry 128 can be included, such as a fuse, filtering electronics, and other charging electronics (such as regulators, inductors, capacitors, etc.) can be used to control or filter power delivery to the capacitor 124.

The charging station 106 is provided to transfer power from a power source, such as a wall receptacle, to the handheld device 100. The charging station 106 includes a housing 130, such as made of plastic, including a receptacle 132 for receiving the handheld device 100 when not in use.

The housing 130 also forms a protective enclosure for charging electronics 134. The charging electronics 134 receive power from a wall receptacle or other power source, through the power cable 136, and converts the power into a form that can be transferred to the handheld device 100. For example, the charging electronics 134 can include an alternating current ("AC") to direct current ("DC") converter for converting the AC from the wall receptacle to a lower voltage DC signal.

In some embodiments the charging electronics include electrical contacts that are shaped to make a direct electrical connection with electrical contacts on the power handle 104 for direct power transfer. In another possible embodiment, the charging electronics 134 include a coil for inductively transferring power to the power handle 104. In some embodiments, the charging electronics 134 includes a constant wattage circuit, which provides energy at a rate equal to the maximum available DC power. As an example, the maximum available DC power is in a range from about 1 W to about 100 W. In another embodiment, the maximum available DC power is about 60 W. Other embodiments have other maximum available DC power values.

In some embodiments the instrument 102 is connected to the power handle 104 at an interface 140. The interface typically includes a mechanical interface, such as mating screw threads, or a snap together connection, and also an electrical interface to transfer power from the power handle 104 into the instrument 102. In some embodiments the instrument 102 can be disconnected from the power handle 104 at the interface. A common interface 140 design can be used in a variety of different types of instruments, to permit a single configuration of power handle 104 to be used with multiple different types of instruments. In other possible embodiments, however, instrument 102 is a single unit that includes the components of the power handle 104 within the housing of instrument 102, rather than within a separate power handle.

Figure 2:
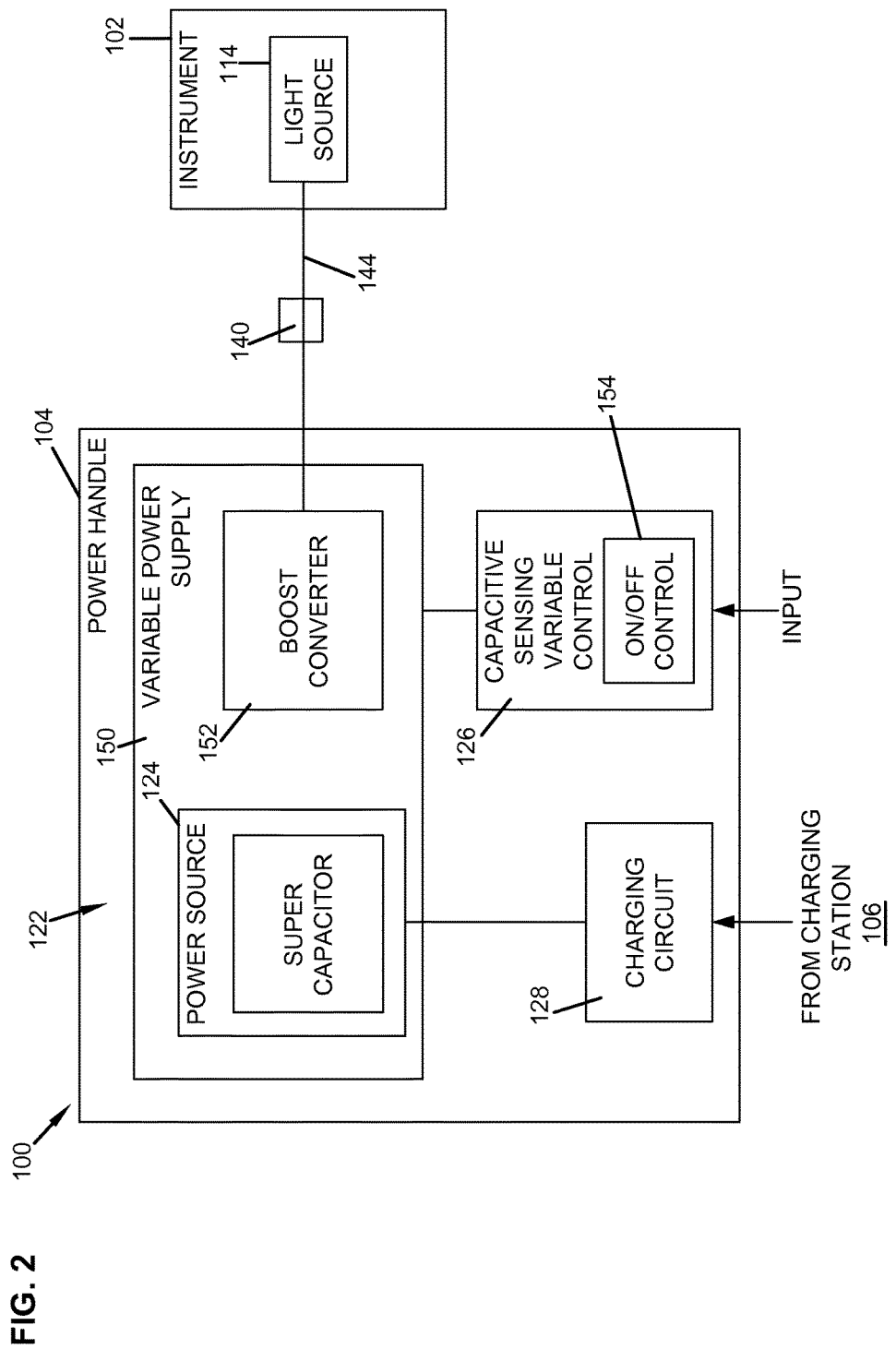
FIG. 2 is an electrical block diagram of the example handheld device, including an instrument and a power handle.

FIG. 2 is an electrical block diagram illustrating an example of the handheld device 100. As shown in FIG. 1, the example handheld device 100 includes an instrument 102 and a power handle 104. In other embodiments, the power handle 104 is integrated with the instrument 100. The instrument 100 typically includes an electronic device, such as a light source 114.

In some embodiments, the electronic circuitry 122 of the power handle 104 provides a substantially constant power and/or substantially constant output voltage to the instrument 102 during operation. In some embodiments, the electronic circuitry 122 provides a power and voltage output that mimics the output of one or more batteries. In some embodiments, the power handle 104 includes, for example, a variable power supply 150, a variable control 126, and a charging circuit 128. The variable power supply 150 typically includes a power source 124, such as including a super capacitor 124.

In some embodiments, the instrument 102 is an electronic instrument including one or more electronic devices requiring electrical power, such as a light source 114. Examples of the light 114 include a halogen bulb and a light emitting diode. Other embodiments include other electronic devices or combinations of electronic devices within the instrument 102. The instrument 102 receives power from the power handle 104 through one or more conductors 144. The conductors 144 pass electrical power through the interface 140 between the power handle 104 and the instrument 102.

The one or more electronic devices of the instrument 102, such as the light 114, require a certain amount of power in order to function in their intended manner. For example, if the voltage supplied to the electronic devices falls below a minimum operating voltage, the electronic devices will no longer function in their intended manner. An example of a minimum operating voltage is 3.5 v for a 3.5 v halogen bulb. Other embodiments have other minimum operating voltages.

In some embodiments, the minimum operating voltage is the minimum voltage required to power the electronic instrument for effective use by a healthcare provider during a patient encounter. Accordingly, the electronic circuitry 122 operates in some embodiments to maintain the voltage at or above the minimum operating voltage, as described in more detail herein. The power handle 104 includes the electronic circuitry 122. In this example, the electronic circuitry 122 includes a capacitor 124, charging circuitry 128, boost converter 152, and on/off control 154.

The length of time that the instrument 102 can be powered by a single charge on capacitor 124 is a function of the power drawn by instrument 102 and the capacity of the one or more capacitors 124. As an example, a capacitor 124 having a capacity of 3,000 Ws can supply 3 W of power to the instrument 102 including a 3 W halogen bulb for about 15 minutes. The same capacitor can supply 1 W of power to an instrument 102 including a 1 W LED bulb for about 50 minutes. As another example, a capacitor 124 having a capacity of 1800 Ws can supply 3 W of power for 10 minutes, and 1 W of power for 30 minutes.

The charging circuitry 128 operates to charge the capacitor 124 when the power handle is placed into the charging station 106 and the charging station 106 is connected to a power source. The power is converted to a form suitable for delivery to the capacitor, which can be charged very rapidly. For example, some embodiments can charge the capacitor 124 from a fully depleted state to a fully charged state in less than one minute.

The charge time is a factor of the power capacity of the capacitor 124 and the rate of power delivery from the charging station 106 to the charging circuitry 128 and into the capacitor 124. As one example, the capacitor 124 has a power capacity of 3,000 Ws, and the charging circuitry 128 can deliver 60 W of power to the capacitor 124. In this example, the capacitor 124 can be charged in 50 seconds. As another example, the capacitor 124 has a power capacity of 1,800 Ws, and the charging circuitry 128 can deliver 60 W of power to the capacitor 124. In this example, the capacitor 124 can be charged in approximately 30 seconds. As a result, even if the handheld device 100 is not put back into the charging station 106 until the capacitor 124 is fully depleted, the handheld device 100 can be fully charged in less than one minute, or charged to a functional state in even less time.

During normal operation, the output of the capacitor 124 has a voltage that decreases rapidly from the initial voltage. Most electronic devices utilized in the instrument 102, such as the light 114, require at least a minimum operating voltage that may not be directly provided by the capacitor 124 after a period of time. If the voltage falls below the minimum operating voltage, the electronic device may cease to operate.

The boost converter 152 is provided to boost the voltage from the capacitor 124 to a desired level so that the electronic devices in the instrument 102 can continue to operate even after the voltage from the capacitor 124 has decreased below the minimum operating voltage. In this example, the boost converter 152 provides a constant voltage output, despite the decreasing voltage from the capacitor 124. An example of the constant voltage output is 3.6 v to power a 3.5 v halogen bulb. Other embodiments provide other voltage outputs.

In some embodiments, the boost converter 152 is an out bound buck-boost circuit that delivers a regulated output voltage until the voltage on the at least one capacitor has dropped to the minimum voltage that the specific electrochemical construction allows. As one example, some embodiments continue to supply the regulated output voltage until the voltage on the at least one capacitor 124 has dropped to approximately 0.5 v.

In this example, an on/off control 154 is provided in addition to the variable control 126 to turn on or off the power handle 104. When the on/off control 154 is in an off position, the power handle 104 does not deliver power to the instrument 102. When in the on position, the power handle 104 delivers power to the instrument 102, so long as adequate power remains in the capacitor 124.

In some embodiments, the operation of the electronic device is variable. For example, the light source 114 is a dimmable bulb, which generates a variable intensity light output depending on the power received from the variable power supply. In some embodiments the light source 114 is adjustable between an off state and a full intensity state by adjusting a voltage supplied to the light source 114. In another embodiment, the light source 114 is adjustable by adjusting a duty cycle of a pulse-width modulated signal supplied to light source 114.

The variable power supply 150 generates an output that is delivered to instrument 102, such as through the interface 140. The output is used to power the light source 114, or other electronic devices in instrument 102. In some embodiments, the variable power supply provides a variable voltage output. In other embodiments, the variable power supply provides a variable power output, such as by pulse-width modulating the output signal.

The variable control 126 receives input from the user, which is passed to the variable power supply 150 and used by the variable power supply 150 to adjust the output. One example of the variable control 126 is shown in FIG. 3, and other examples are illustrated and described herein.

Some embodiments include charging circuit 128 that operates to charge the power source 124 when the power handle is placed into a charging station or plugged into a charging cord. The charging station or charging cord typically receives power from a wall receptacle. The charging circuit 128 converts the power into a form suitable for delivery to the power source 124.

Figure 3:
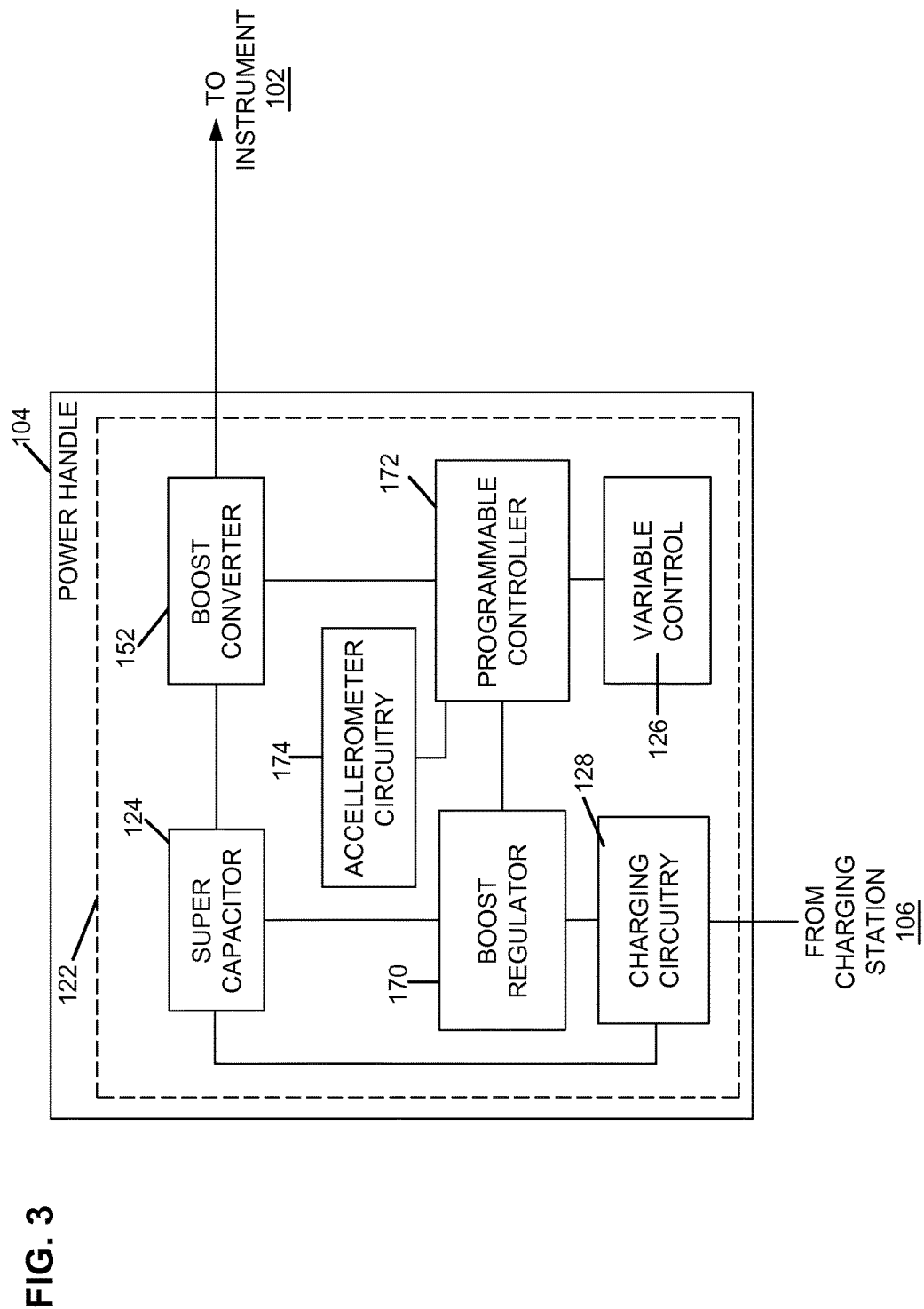
FIG. 3 is an electrical block diagram illustrating another example of the power handle shown in FIG. 2.

FIG. 3 is an electrical block diagram illustrating another example of the power handle 104. In this example, the power handle 104 includes electronic circuitry 122 including a capacitor as power source 124, a variable control 126, charging circuitry 128, and a variable power supply 150. In this example, the variable power supply includes a boost converter 152, a boost regulator 170, and a programmable controller 172. In this example, the power handle 104 provides a user variable power and/or a user variable output voltage to instrument 102 during operation, such as to permit the intensity of the light 114 (shown in FIG. 1) to be adjusted.

In this example, the power source 124, charging circuitry 128, and boost converter 152 all operate as described with reference to FIG. 2, except that the boost converter 152 is configured to receive an input from the programmable controller 172, and to adjust the output voltage accordingly.

The variable power supply 150 receives power from power source 124, such as one or more super capacitors. A voltage at a capacitor decreases rapidly over time, and can quickly be reduced to below a minimum operating voltage required to power the instrument 102. (In another possible embodiment, described herein, the power source 124 includes electronics that adjust the output characteristics of the capacitor, such as to mimic the output characteristics of a battery, or multiple batteries.)

Accordingly, in this example the variable power supply 150 includes a boost converter 152 that boosts the voltage from the capacitor 124 to a desired level so that the electronic devices in the instrument 102 can continue to operate even after the voltage from the capacitor 124 has decreased below the minimum operating voltage.

In some embodiments, the boost converter 152 is an out bound buck-boost circuit that delivers a regulated output voltage until the voltage on the at least one capacitor has dropped to the minimum voltage that the specific electrochemical construction allows. As one example, some embodiments continue to supply the regulated output voltage until the voltage on the at least one capacitor 124 has dropped to approximately 0.5 v.

The variable control 126 receives input from the user, such as a healthcare provider, to turn the power handle 104 on and off, or adjust the output of the power handle 104. The variable control 126 also receives inputs from the user that indicate a desire for the power to the instrument 102 to be increased or decreased. The input from variable control is provided to the programmable controller 172.

The boost regulator 170 receives power from the capacitor 124 and modifies the power into a form required by the programmable controller 172, such as having a substantially constant fixed voltage. This power is then supplied to the programmable controller 172 to support the proper operation of the programmable controller 172.

The programmable controller 172 operates as an intelligent controller for the power handle 104. In some embodiments, data instructions are stored in a memory device, which may be a part of the programmable controller 172 (e.g., on-board memory) or a separate memory device that is readable by the programmable controller 12. The data instructions are executed by the programmable controller 172 to perform operations defined by the data instructions.

Figure 5:
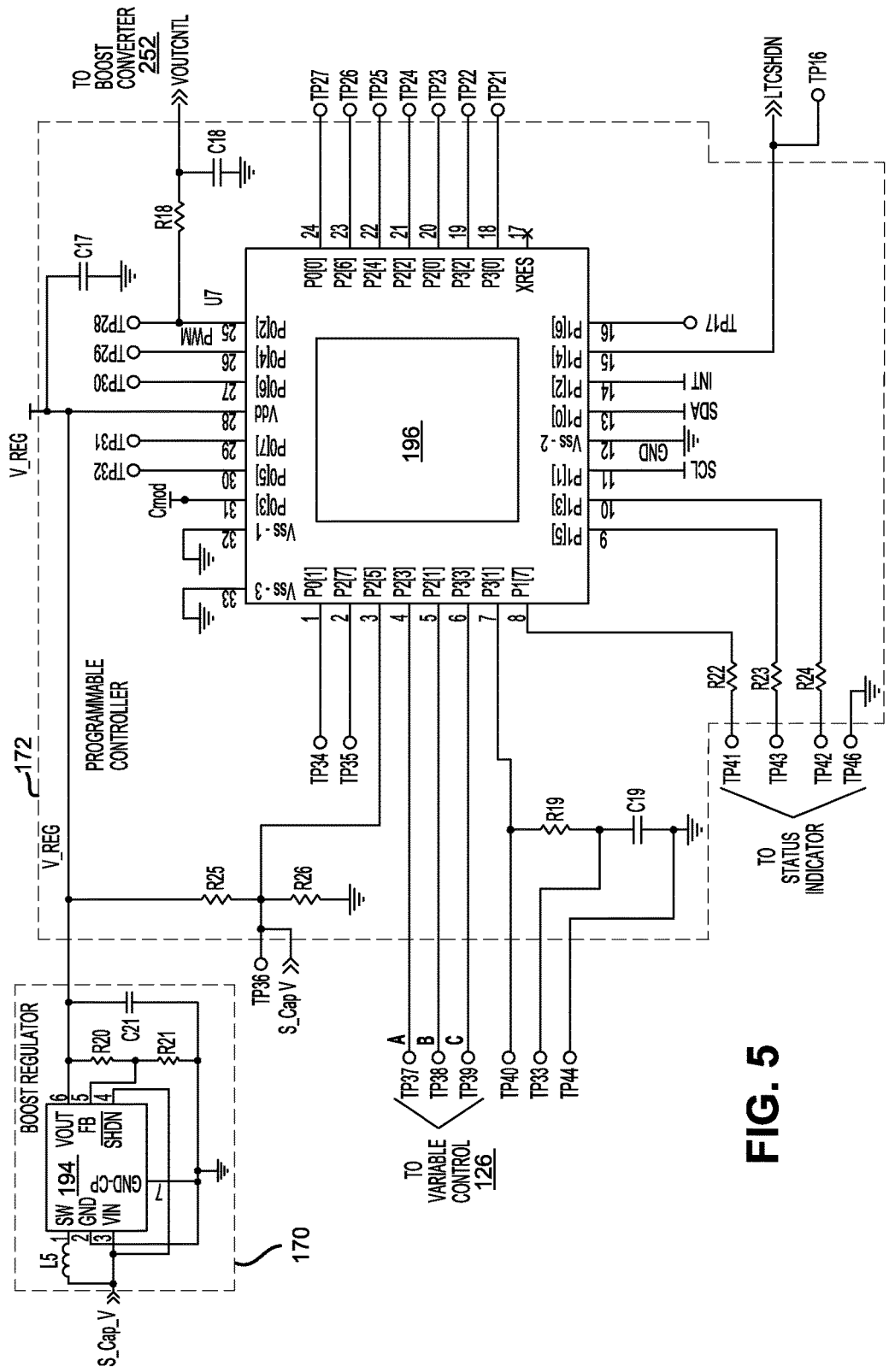
FIG. 5 is an electrical schematic of an example boost regulator and a programmable controller of the example power handle shown in FIG. 3.

One example of the programmable controller 172 is shown in FIG. 5, which includes a processing device. Examples of processing devices include microprocessors, central processing units, microcontrollers, programmable logic devices, field programmable gate arrays, digital signal processing devices, and the like. Processing devices may be of any general variety such as reduced instruction set computing devices, complex instruction set computing devices, or specially designed processing devices such as an application-specific integrated circuit device.

The programmable controller 172 receives user input from the variable control 126, and operates in conjunction with the boost converter 152 to generate a user variable output to the instrument 102. The boost converter 152 compensates for the decreasing voltage of the capacitor over time, while the programmable controller 172 provides inputs to the boost converter 152 to adjust the output power to the level desired by the healthcare provider.

Figure 10:
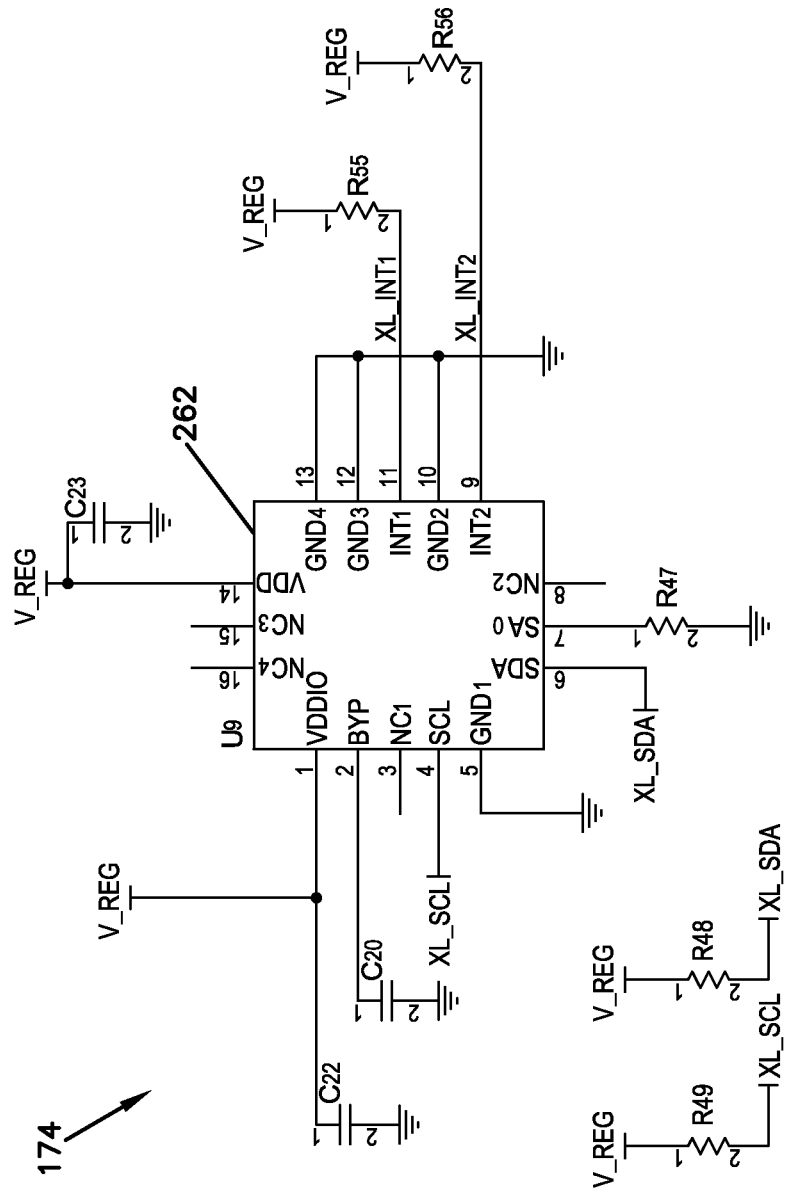
FIG. 10 is a schematic diagram illustrating an example of the accelerometer circuitry.

Some embodiments include accelerometer circuitry 174. An example of the accelerometer circuitry 174 is shown in FIG. 10, and includes at least an accelerometer. In some embodiments, the accelerometer detects an orientation of the power handle 104 with respect to the earth, and movement of the power handle 104. In some embodiments, the accelerometer detects orientation and movement in three axes, including a vertical axis and two perpendicular horizontal axes. In some embodiments, the accelerometer provides orientation and acceleration information relating to three dimensions.

Figure 4:
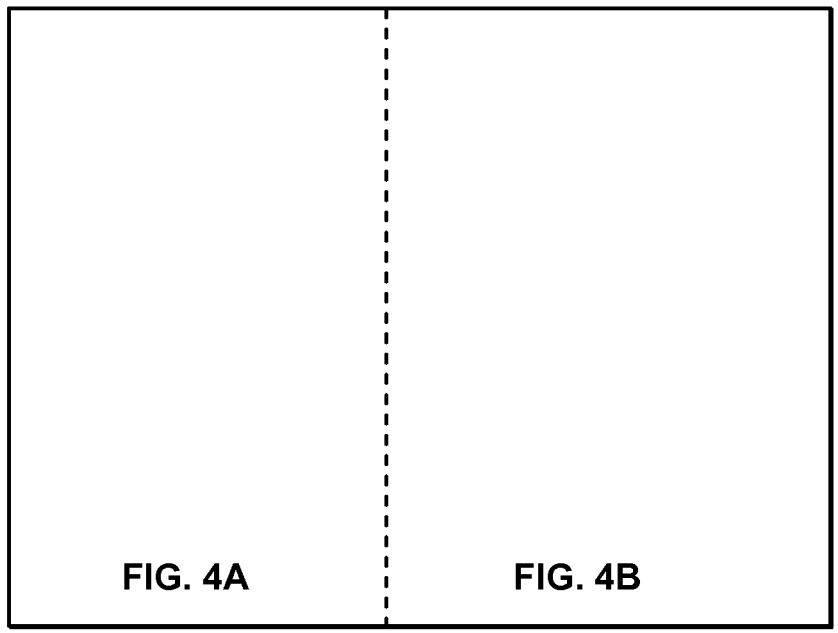
FIG. 4 illustrates an arrangement of FIGS. 4A and 4B.

FIGS. 4-5 illustrate a more detailed example of the power handle 104 shown in FIG. 3.

Figure 4A:
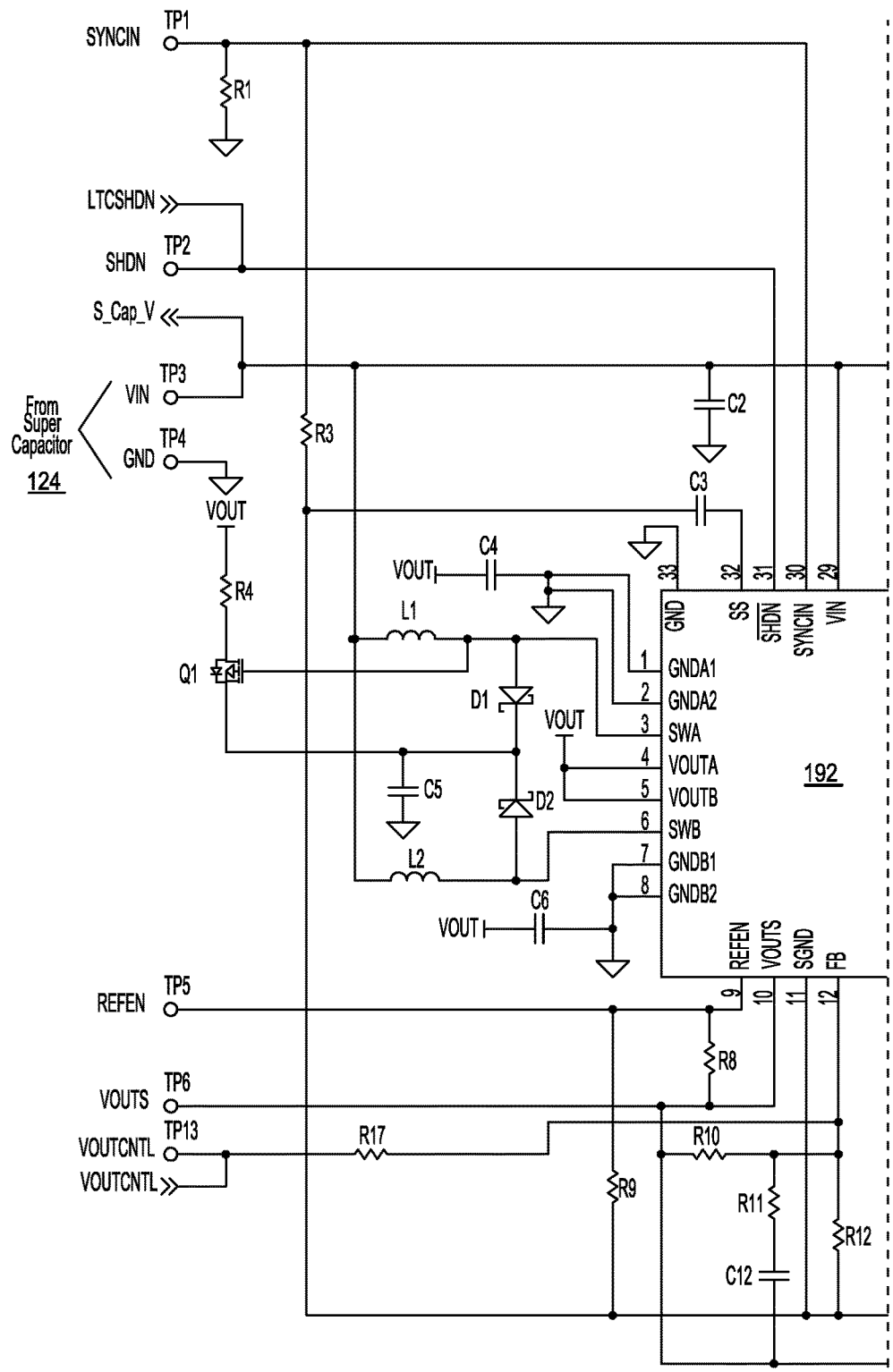
FIG. 4A is a first portion of an electrical schematic of an example boost converter of the example power handle shown in FIG. 3.
Figure 4B:
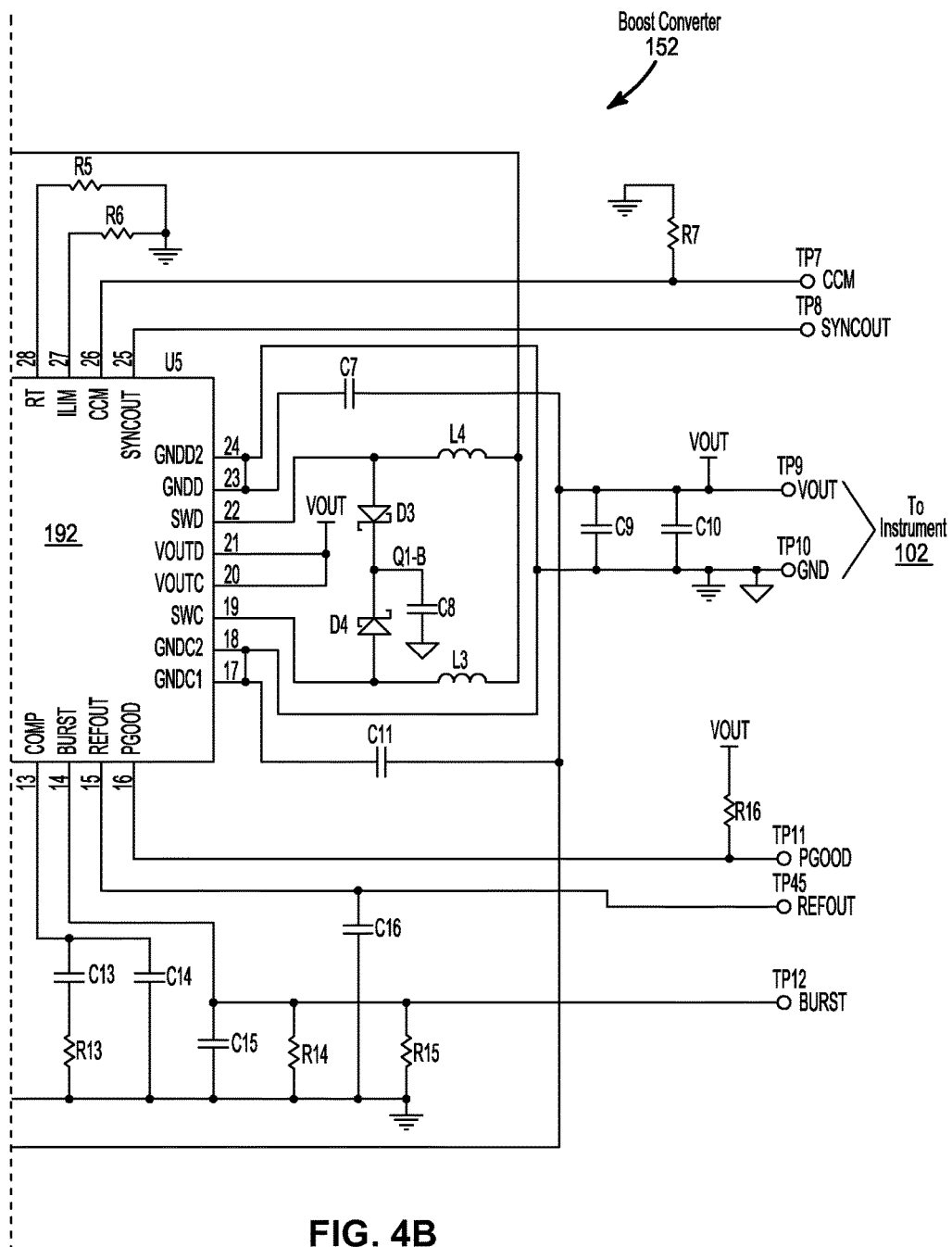
FIG. 4B is a second portion of the electrical schematic shown in FIG. 4A.

FIG. 4 (including FIGS. 4A and 4B) is an electrical schematic of an example boost converter 152 of the electronic circuitry 122 shown in FIG. 3. The boost converter 152 includes an integrated circuit 192, circuit points TP1 to TP12, inductors L1-L4, Schottky diodes D1 to D4, capacitors C1 to C16, resistors R1 to R15, and a metal oxide semiconductor field effect transistor (MOSFET) Q1.

The integrated circuit 192 is, for example, a 4-phase synchronous step-up DC/DC converter, such as Part No. LTC3425 distributed by Linear Technology Corporation of Milpitas, Calif. Other converters are used in other embodiments.

Power is received from the capacitor 124 at circuit point TP3, which is supplied to inductors L1, L2, L3, and L4, through Schottky diodes D1, D2, D3, and D4, and output by MOSFET Q1. The integrated circuit 192 detects the voltage being supplied by the capacitor and controls the switching of the circuit such that the voltage is increased across the inductors L1, L2, L3, and L4 to the desired level.

In this example, the boost converter 152 is also configured to receive an input from the programmable controller 172, shown in FIG. 5, to provide a user variable output voltage. The input is received by the boost converter 152 at the circuit point TP13 and is labeled as VOUTCNTL.

The output of the circuit at circuit point TP9, which is labeled as VOUT, is then provided to instrument 102.

FIG. 5 is an electrical schematic of an example circuit including a boost regulator 170 and a programmable controller 172. In this example, the boost regulator 170 includes an integrated circuit 194, an inductor L5, resistors R20 and R21, and a capacitor C21. The example programmable controller 172 includes a processing device 196, circuit points TP16 to TP46, resistors R18 to R26, and capacitors C17 and C18.

The integrated circuit 194 is, for example, a synchronous step-up dc/dc converter, such as Part No. LTC3526LB distributed by Linear Technology Corporation. The boost regulator 170 is coupled to the capacitor 124 at the circuit point labeled as S_CAP_V, and operates to generate a substantially constant fixed voltage output (labeled as VREG) as needed to operate the programmable controller 172.

The programmable controller 172 includes a processing device 196. An example of the processing device 196 is a programmable system-on-chip, such as Part No. CY8C21434 distributed by Cypress Semiconductor Corporation of San Jose, Calif. The programmable system-on-chip includes a CPU and memory devices. The memory devices include static random access memory (SRAM), static read only memory (SROM), flash memory. The programmable controller 172 can also include a variety of other devices, such as clocks, input/output interfaces, digital and analog electronics, etc.

The programmable controller 172 receives inputs from the variable control 126 at circuit points TP37, TP38, and TP39, and generates an appropriate output signal that is provided to the boost converter 152, at the circuit point labeled as VOUTCNTL. Circuit points TP37, TP38, and TP39 are inputs to the capacitance sensors provided by the programmable system-on-chip, where the inputs are received from the variable control 126. In one example, the circuit point TP37 is an input to a capacitance sensor A, the circuit point TP38 is an input to a capacitance sensor B, and the circuit point TP39 is an input to a capacitance sensor C.

In this example, the power handle 104 includes a status indicator, such as a light emitting diode (LED) indicator. The status indicator is operable to illuminate with a specific color indicative of a status of the power handle. In one example, the status indicator is a single indicator having three integral LEDs, including a red LED, a green LED, and a blue LED. The LEDs are operated by the programmable controller 172 to indicate the status. For example, a yellow status light indicates that the power handle 104 is in need of charging, a blue status light indicates that the power handle is charging, and a green status light indicates that the power handle 104 is fully charged.

In some embodiments, the example circuit shown in FIG. 5 also includes accelerometer circuitry 174. An example of the accelerometer circuitry 174 is shown in FIG. 10.

Further, the devices are compatible with other 3.5 v powered products in the market, including both LED and Halogen powered devices.

Using super capacitors instead of batteries offering nearly a lifetime of charge cycles (>50,000) without filling the land fill with old batteries and in addition offers the ability to charge in about less than one minute improving workflows and overall reliability and availability. The devices are also compatible with charging off the USB 2.0 connections. It can be charged using the Welch Allyn 5 watt platform power supply, for example.

The handles for the devices have an improved user interface ("UI") offering up to 360 degree visual of remaining energy status, and ON/OFF when lifted from rest or put down for maximum energy conservation.

The handles also allow for dimming control using no moving parts enabling a sealed unit for improved cleaning and overall reliability.

The devices (or Battery-Free Green Series) come on to full brightness when lifted up instantly. When any surface on a blue touch point is covered with a thumb, the handles automatically begin to dim down in a controlled rate of approximately three seconds. When, for example, the thumb is lifted, the intensity will remain where it was at that moment. If the thumb is put over the touch point again, the intensity reverses direction upwards at the same rate and will again freeze at the point the thumb is lifted. It will continuously reverse intensity each time it is "touched."

If the Battery-free Green series handle senses more than one finger over the touch point, such as in a position when an Otoscope is used, the intensity freezes at that moment.

The Battery-Free Green Series automatically senses whether a Halogen bulb or LED bulb is installed upon every power up cycle and adjusts the output voltage range for maximum linearity when dimming.

The handle will glow green when the energy is in about the top 20 percent of capacity and will blink amber when it is at about the bottom 20% of the remaining energy range. It will be off otherwise.

In the AC charging station, it will take less than about one minute to completely charge.

In the USB charging station, whether it is hooked up to a computer or to the 5 watt charger, it will take less than about 1 hour to completely charge.

Using a travel charger, it will take less than about eight hours to charge.

Both the AC and 5 watt chargers are designed and built to meet Energy Star 2.0 standards for the maximum energy efficiency both when in use and in stand by modes.

The Battery-free handles are completely maintenance free and may not require service ever.

The charging stations can be configured as single handle chargers or dual handle versions. They will also be compatible with many devices including future Welch Allyn handheld devices.

Figure 6:
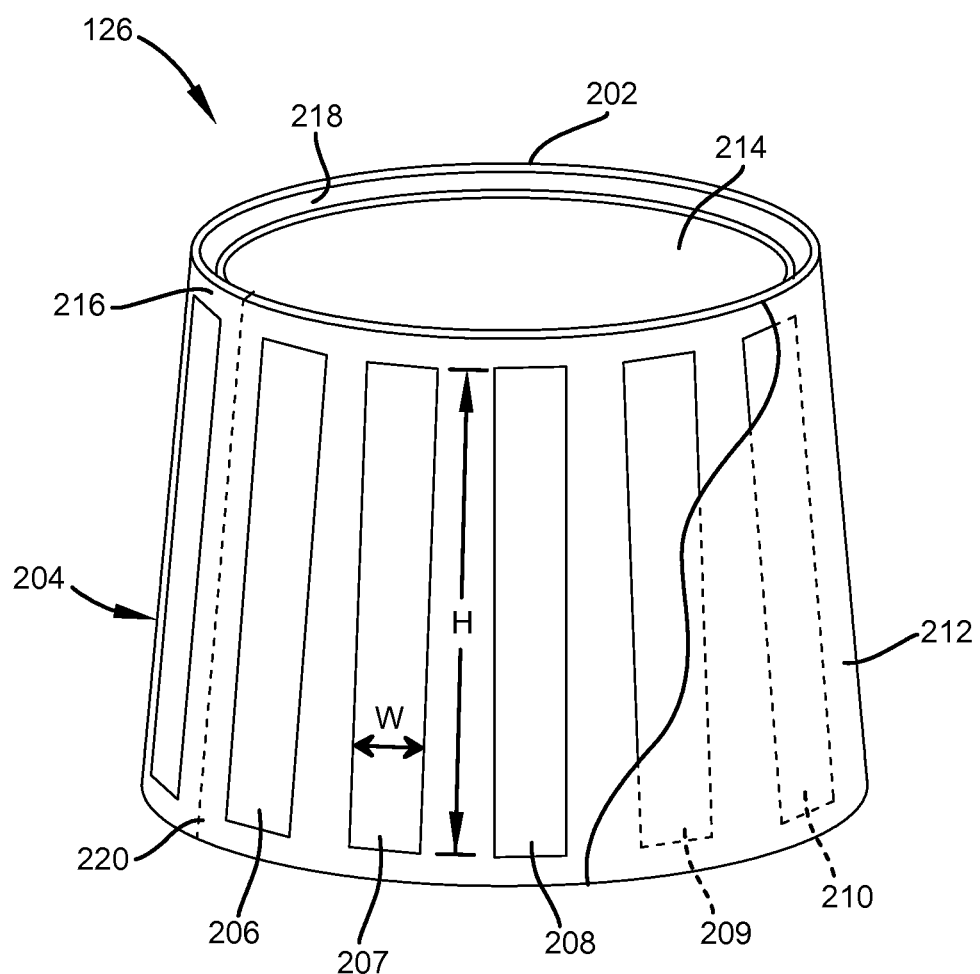
FIG. 6 is a perspective view of an example variable control of the handheld device shown in FIG. 1.

FIG. 6 is a perspective view of an example variable control 126. In this example, variable control 126 includes a flexible circuit board 202, electrical conductors 204, an insulating layer 212, and a conductive layer 214. The flexible circuit board 202 includes an outer surface 216 and an inner surface 218.

In some embodiments the circuit board 202 is formed of a flexible material. The material is typically manufactured in a flat shape, but can be bent into a desired shape, such as shown in FIG. 6. Ends of the circuit board 202 can be fastened together to form a joint 220, with any suitable fastener, such as a clip, adhesive, solder or weld joints, or other fasteners. Some embodiments are bent and joined together at joint 220 to form a circuit board 202 having a substantially circular cross section. The circuit board 202 is typically made from a substrate, such as a flexible plastic. The flexible circuit board 202 includes an insulating material, and can further include conductive traces formed on or within the insulating material. Additional electronic components can be formed on or fastened to the flexible circuit board 202. In some embodiments the circuit board 202 is rigid and substantially inflexible. In some embodiments the circuit board 202 is molded into the desired shape.

In this example, electrical conductors 204 are formed on outer surface 216 of the flexible circuit board 202. An example of a conductive material suitable for electrical conductors 204 is copper. Gold or other suitable metals or conductive materials are used in other embodiments. The electrical conductors include conductors 205, 206, 207, 208, 209, 210, and other electrical conductors. Some embodiments include a quantity of electrical conductors 204 in a range from about 3 to about 50, and preferably from about 9 to about 18. One example includes 12 conductors 204.

The electrical conductors 204 are in the form of elongated strips, having a thickness, a width, and a height. Different embodiments can have different dimensions. As one example, the width W of the electrical conductors 204 is in a range from about 0.01 inches to about 0.25 inches. In another example, the width W is in a range from about 0.1 inches to about 0.15 inches. The height H of the electrical conductors 204 is in a range from about 0.5 inches to about 2 inches. In another example, the height H is in a range from about 0.7 inches to about 1.3 inches. Other embodiments have other dimensions. An example of the thickness of the conductor 204 is in a range from about 0.001 inches to about 0.05 inches. Other embodiments have other dimensions.

An insulating layer 212 is formed over electrical conductors 204 and the outer surface 216 of circuit board 202. In some embodiments the insulating layer 212 is a coating. In other embodiments, insulating layer 212 is a separate layer of material that is placed adjacent to outer surface 216 of circuit board 202. The insulating layer 212 forms at least a portion of housing 120 that protects and encloses the variable control 126.

Some embodiments include a conductive layer 214 formed on the inner side 218 of circuit board 202. The conductive layer 214 is separated from electrical conductors 204 by the insulating circuit board 202. In this way, the conductors 204 and the spaced conductive layer 214 form a plurality of capacitors distributed around the circuit board 202. In some embodiments the conductive layer 214 is a ground plane.

Figure 7:
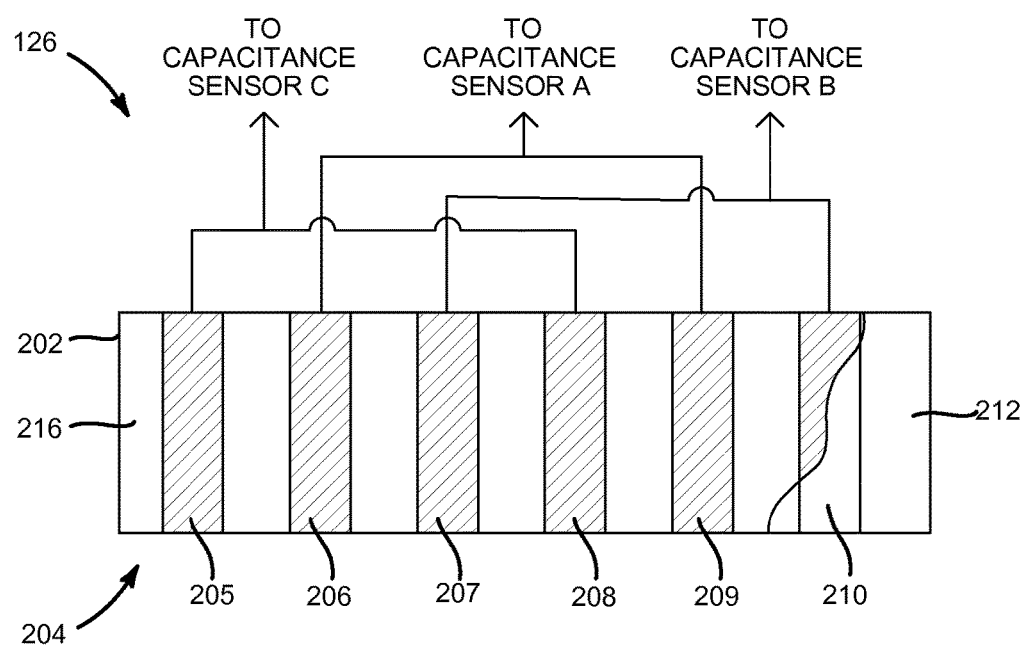
FIG. 7 is a plan view of another example variable control.

FIG. 7 is a plan view of another example variable control 126. In this example, the variable control 126 is formed of a substantially flat circuit board 202. In some embodiments the circuit board 202 is flexible and can be bent to have a substantially circular cross-sectional shape, or into another shape, as desired. In another embodiment, the circuit board 202 is substantially rigid, and maintains a substantially flat shape. For example, a straight circuit board can be included within a flat region of a device's housing, such as the top, side, or back of a mobile phone.

The variable control 126 shown in FIG. 7 includes features similar to that shown in FIG. 6, such as the electrical conductors 204 provided on the outer surface 216 of circuit board 202, an insulating layer 212 adjacent the electrical conductors 204, and in some embodiments a conductive layer (not visible in FIG. 7) along the rear surface of circuit board 202. Additional electronic components and electrical traces are included in some embodiments.

FIG. 7 also illustrates electrical connections between electrical conductors 204 and capacitance sensors. Although some embodiments include a separate capacitance sensor for each electrical conductor 204, the number of capacitance sensors can be reduced by connecting multiple electrical conductors 204 into a single capacitance sensor. In this example, three capacitance sensors are used, labeled as A, B, and C. More specifically, in this example capacitance sensor A is connected to conductors 206 and 209, capacitance sensor B is connected to conductors 207 and 210, and capacitance sensor C is connected to conductors 205 and 208. Additional conductors are included in some embodiments, and the additional conductors can be similarly connected to the capacitance sensors A, B, and C in an alternating fashion as shown in FIG. 7. By using at least three capacitance sensors, the direction of movement can be detected, as discussed with reference to FIG. 8.

Figure 8:
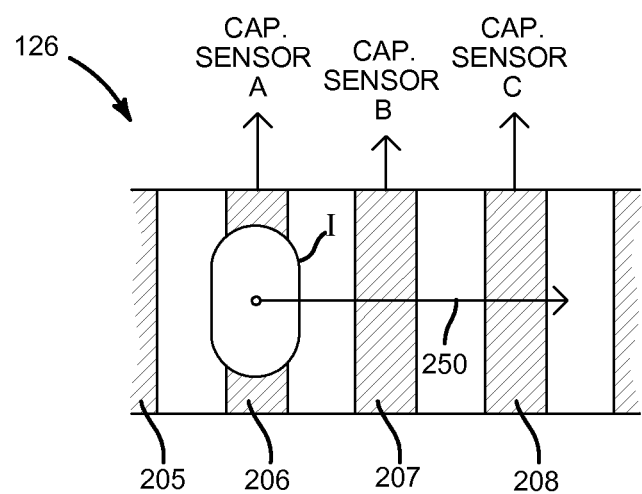
FIG. 8 is a plan view of the example variable control shown in FIG. 7, which illustrates the receipt of an input from a user.

FIG. 8 is a schematic block diagram of an example variable control 126 illustrating the receipt of an input from a user. An insulating layer 212 of the housing 120 is not shown in FIG. 8 in order for the electrical conductors 204 to be visible.

A user provides an input I to the variable control 126 by placing a finger on the housing in the vicinity of the variable control 126, such as adjacent to the conductor 206. Upon doing so, the capacitance sensor A detects a change in the capacitance at the conductor 206. For example, an increased capacitance is detected.

The user then moves the finger across the variable control 126 in the direction of arrow 250. As the input I from the finger moves away from conductor 206, the capacitance sensor A detects a decrease in the capacitance, while the capacitance sensor B detects an increase in capacitance at conductor 207. If the input continues in the direction of arrow 250, the capacitance sensor B detects a decrease in the capacitance as the input I from the finger moves beyond conductor 207 and toward conductor 208, at which time the capacitive sensor C detects an increase in capacitance.

Figure 9A:
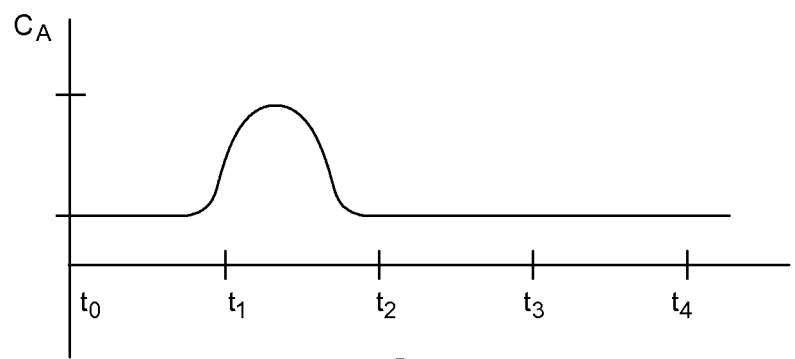
FIG. 9A is a first schematic diagram illustrating the detected capacitances at several capacitance sensors upon receipt of the input shown in FIG. 8.
Figure 9B:
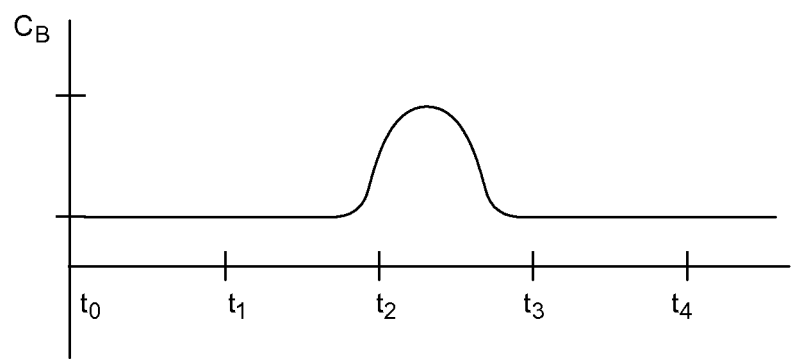
FIG. 9B is a second schematic diagram illustrating the detected capacitances at several capacitance sensors upon receipt of the input shown in FIG. 8.
Figure 9C:
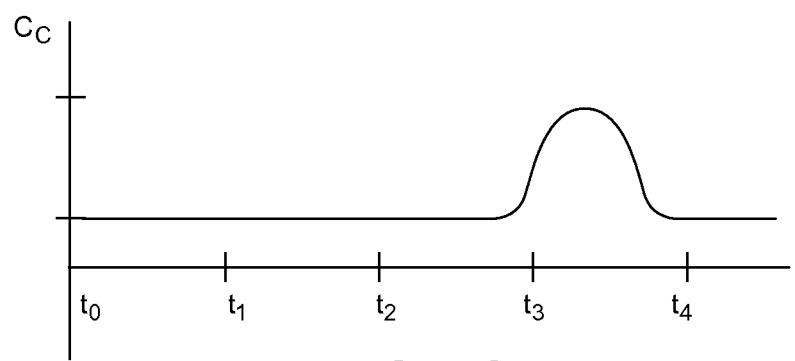
FIG. 9C is a third schematic diagram illustrating the detected capacitances at several capacitance sensors upon receipt of the input shown in FIG. 8.

FIG. 9 (including FIGS. 9A-9C) is a schematic diagram illustrating the detected capacitances at each capacitance sensor upon receiving an input I as shown in FIG. 8. Three graphs are illustrated in FIG. 9, which show the capacitance detected by three difference capacitance sensors over the same period of time. The first graph (FIG. 9A) shows the capacitance detected by a capacitance sensor A ($C_A$), the second graph (FIG. 9B) shows the capacitance detected by a capacitance sensor B ($C_B$), and the third graph (FIG. 9C) shows the capacitance detected by a capacitance sensor C ($C_C$).

At time $t_0$, no input is being provided to the variable control 126, and so capacitance sensors CA, CB, and CC all detect approximately the same nominal capacitance, which is, for example, the sum of the capacitances between each conductor 204 connected to the respective capacitance sensor, and the conductive layer 214 along a rear surface of the circuit board 202 (e.g., shown in FIG. 6).

At time $t_1$, the input I is provided to the variable control 126, in which the user places a finger on the variable control 126 adjacent to conductor 206, as shown in FIG. 8. The presence of the finger causes capacitance sensor A to detect an increase in the capacitance at time $t_1$.

The user then moves the finger in the direction of arrow 250, shown in FIG. 8. The input I is detected by capacitance sensor A as a decrease in capacitance, but as an increase in capacitance by capacitance sensor B. As a result, at time $t_2$ the capacitance has returned to the nominal level at capacitance sensor A, but has increased at capacitance sensor B. As a result, the movement can be determined by the processor to be in the direction of arrow 250.

If the movement continues in the direction of arrow 250, the capacitance sensor B detects a decrease in capacitance, while the capacitance sensor C detects an increase in capacitance. When the finger is adjacent conductor 208 at time $t_3$, the capacitance detected by capacitance sensor B has returned to the nominal level, while the capacitance at capacitance sensor C has increased. The movement is determined by the processor to have continued in the direction of arrow 250, by determining the order in which the capacitance sensors detect an increase in capacitance. For example, A, B, and then C. Similarly, any input that proceeds in the order of A to B, B to C, or C to A, will correctly be identified as being in the direction of arrow 250.

The finger is then removed from the variable control 126, causing all capacitance sensors to detect a nominal capacitance at time $t_4$.

The variable control can similarly receive an input I in the opposite direction as arrow 250. For example, an input can be provided by placing a finger adjacent conductor 208, and then moved across conductors 207, and then conductor 206. In this case, the capacitance will be detected in the order of C, B, and then A. Similarly, any input that proceeds in the order of C to B, B to A, or A to C will be correctly identified as being in the opposite direction as arrow 250.

The input I detected by the capacitance sensors is then utilized to adjust the operation of the device 100. For example, the input is used in some embodiments to adjust the power or voltage output from variable power supply 150.

The speed of the input I is also detected in some embodiments. The speed of movement can be determined by the amount of time between transitions, for example, the difference between time $t_1$ and time $t_2$. In some embodiments, a faster movement causes the variable power supply 150 to make a larger magnitude adjustment in to the output, and a slower movement causes the variable power supply 150 to make a smaller magnitude adjustment in the output.

In some embodiments, the direction of a first input I that is received from a user sets an increase direction for that use. For example, if a first input I is in the direction of arrow 250, shown in FIG. 8, the direction of arrow 250 is set as an increase direction. If further input is received in the direction of arrow 250, the output is further increased. If further input is received in the direction opposite arrow 250 (e.g., a decrease direction), the output is decreased.

On the other hand, if the first input I is in the direction opposite arrow 250, that direction is set as the increase direction. Further input received in the direction opposite arrow 250 causes the output to be increased. If further input is received in the direction of arrow 250 (e.g., the decrease direction), the output is decreased. In some embodiments the input direction is reset when the device is turned off (e.g., by providing one or more inputs in the decrease direction, by returning the device to a charging station, or by selecting an off button).

FIG. 10 is a schematic diagram illustrating an example of the accelerometer circuitry 174, shown in FIG. 3.

The accelerometer circuitry 174 includes at least an accelerometer 262. In some embodiments, the accelerometer 262 detects an orientation of the power handle 104 or instrument 100, with respect to the earth, and movement of the power handle 104 or instrument 100. In some embodiments, the accelerometer 262 detects orientation and movement in three axes, including a vertical axis ("z-axis") and two perpendicular horizontal axes ("x-axis" and "y-axis"). In some embodiments, the accelerometer 262 provides orientation and acceleration information relating to three dimensions.

One example of a suitable accelerometer 262 is the 3-Axis, 10-bit/8-bit Digital Accelerometer having model number MMA8453Q, available from Freescale Semiconductor, Inc. of Austin, Tex.

In some embodiments, the accelerometer circuitry 174 utilizes a two-wire interface (such as an Inter-Integrated Circuit ("I²C") bus) to communicate orientation and movement data to the processing device 196, shown in FIG. 5. The two-wire interface utilizes, for example, the I²C serial clock (SCL) pins conductors (also labeled as XL_SCL) and the I²C serial data (SDA) pins and conductors (also labeled as XL_SDA). The two-wire interface connections are also shown in FIG. 5, which are similarly labeled as SCL and SDA, to permit communication between the processing device 196 (FIG. 5) and the accelerometer 262 (FIG. 10).

In some embodiments, the accelerometer 262 provides one or more of the following features: (1) freefall or motion detection, (2) transient detection (i.e., fast motion, jolt), (3) orientation with set hysteresis and z-lockout, (4) shake detection through motion threshold, and (5) single, double, triple, and directional tap detection. Any one or more of these features can be used to provide enhanced techniques for receiving inputs and interacting with the user.

Figure 11:
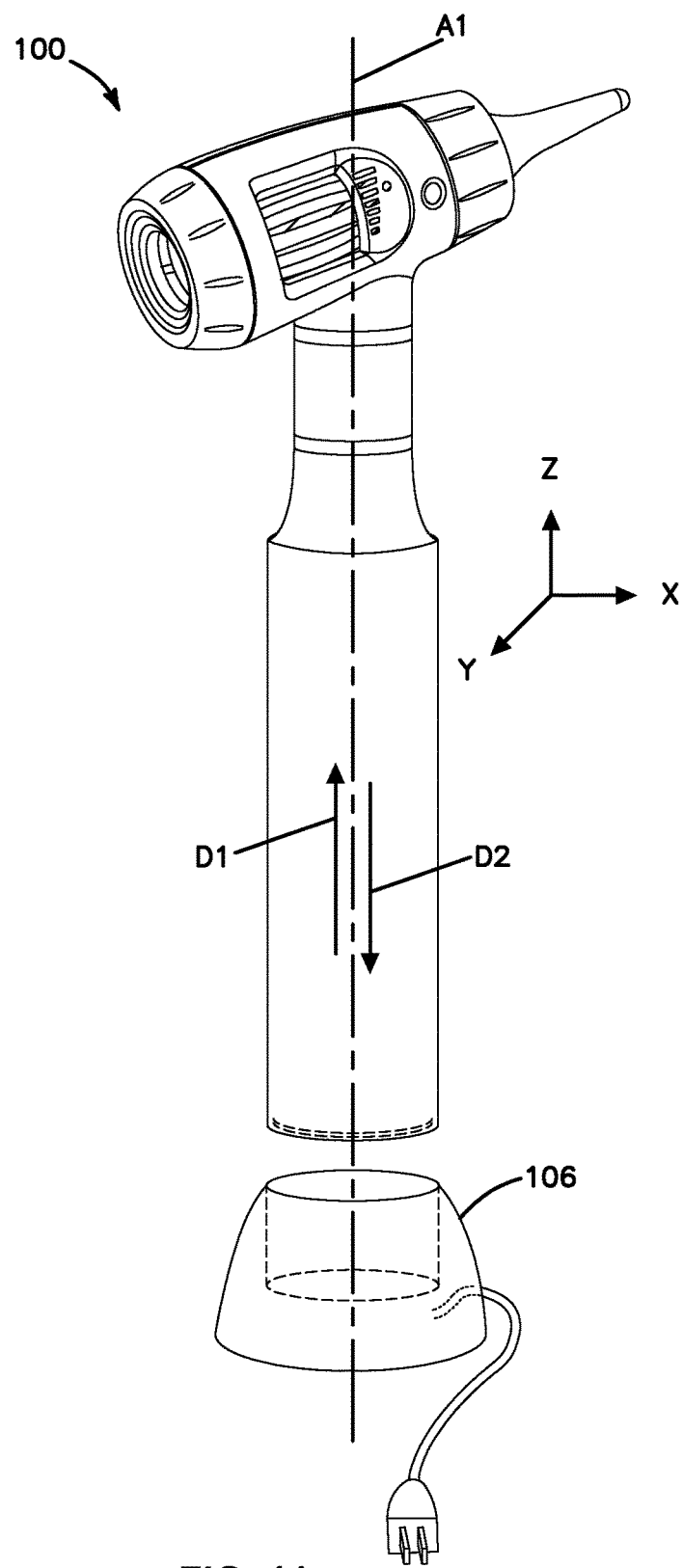
FIG. 11 illustrates several exemplary operations that can be performed by a handheld device.

FIG. 11 illustrates several exemplary operations that can be performed by the instrument 100 utilizing the accelerometer 262 (shown in FIG. 10). FIG. 11 illustrates an example instrument 100 and associated charging cradle 106.

In some embodiments, the instrument 100 operates to automatically turn on when removed from the charging cradle 106, and to automatically turn off when returned to the charging cradle 106.

When the instrument 100 is in the charging cradle 106, for example, the instrument is typically held in a substantially vertical orientation. The instrument 100 does not typically need to be operating when in the charging cradle, and so in this example the instrument 100 is turned off. However, when the instrument 100 is removed from the charging cradle, it is likely that the user will want to use the instrument 100 at that time. As a result, some embodiments operate to detect when the instrument 100 is removed from the charging cradle 106 by lifting the instrument 100 in a substantially vertically upward direction (direction D1). Upon detection of this movement, the instrument 100 turns on.

Similarly, if the instrument is returned to the charging cradle 106, it is likely that the user no longer desires to use the instrument 100 at that time. Accordingly, in some embodiments the instrument 100 detects the insertion of the instrument 100 into the charging cradle by detecting a substantially vertically downward movement (direction D2). Upon detection of this movement, the instrument 100 turns off.

In some embodiments, the orientation of the instrument 100 is determined using the accelerometer 262. In the illustrated example shown in FIG. 11, the instrument 100 is oriented substantially vertically upward, such that a longitudinal axis (A1) of the instrument 100 is substantially aligned in the vertical (z-axis) direction. Other orientations are also possible. For example, the instrument 100 can also be laid on a flat surface, and arranged so that the longitudinal axis A1 is oriented to be substantially aligned in a first horizontal (x-axis) direction, or in a second horizontal (y-axis) direction. The instrument 100 axis A1 can further be oriented at least partially in any two or more of these directions (i.e., in any direction in three-dimensions).

Additional operations and functions that can be performed by an instrument 100 utilizing data obtained from an accelerometer are illustrated and described in more detail with reference to FIGS. 12-15.

Figure 12:
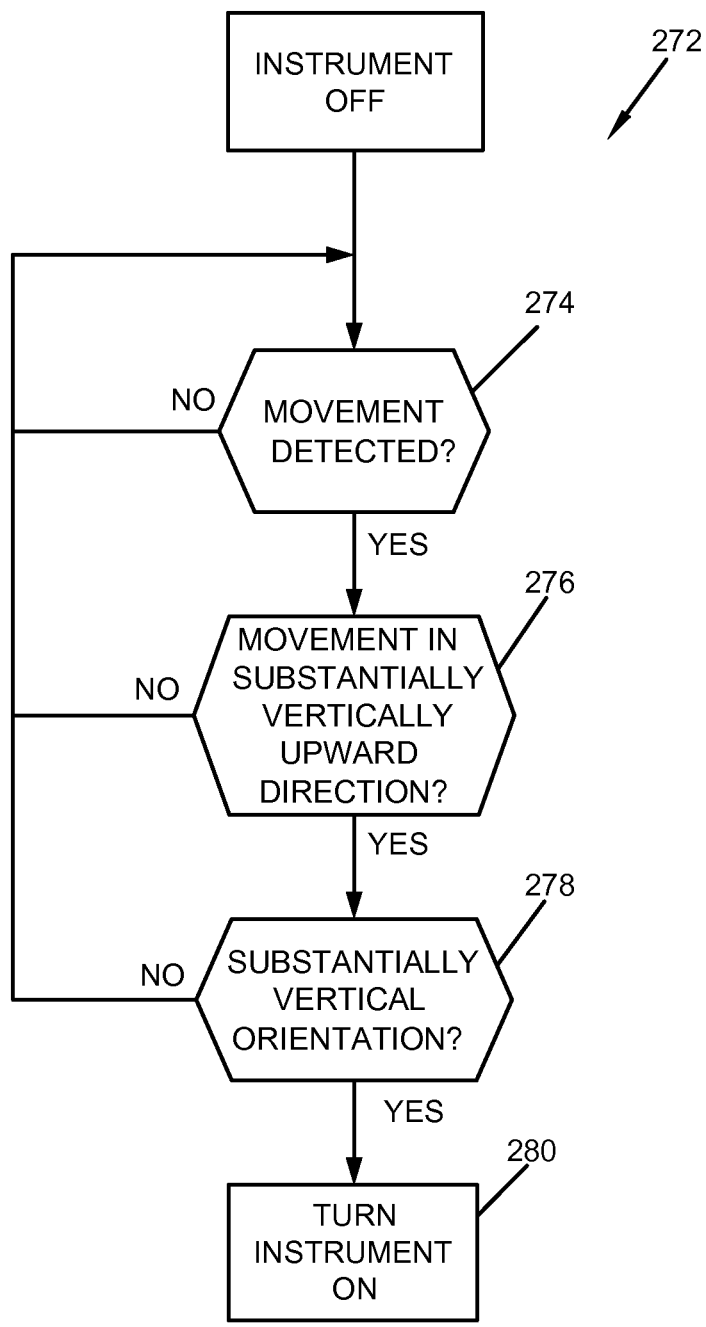
FIG. 12 is a flow chart illustrating an example method of turning ON an instrument.

FIG. 12 is a flow chart illustrating an example method 272 of turning ON an instrument 100. In this example, the method 272 includes operations 274, 276, 278, and 280.

The method 272 begins, in this example, when the instrument 100 is turned OFF. In some embodiments, when the instrument is turned off, it is operating in a lower power sleep mode.

The operation 274 is performed to detect movement, such as using the accelerometer 262, shown in FIG. 10.

When movement is detected, operation 276 is performed to determine if the movement detected in operation 274 matches one or more predetermined directions, such as a substantially vertically upward direction. For example, the operation 276 determines whether the movement is in the direction D1, shown in FIG. 11. The predetermined direction is, for example, the direction that the instrument 100 would need to move in order to be removed from the charging cradle 106, when the charging cradle 106 is placed on a horizontal surface, such as a desk or counter top, or mounted to a vertical wall, for example.

Operation 278 is performed to determine if the orientation of the instrument 100 matches one or more predetermined orientations, such as a substantially vertical orientation. The predetermined orientation is, for example, the orientation of the instrument 100 that is required in order to remove the instrument 100 from the charging cradle 106, when the charging cradle is placed on a horizontal surface, such as a desk or counter top, or mounted to a vertical wall, for example.

If the results of operations 274, 276, and 278 (which can be performed any desired order) are all "YES," the instrument determines that the instrument 100 is being removed from a cradle, and therefore automatically turns the instrument 100 ON in operation 280.

Figure 13:
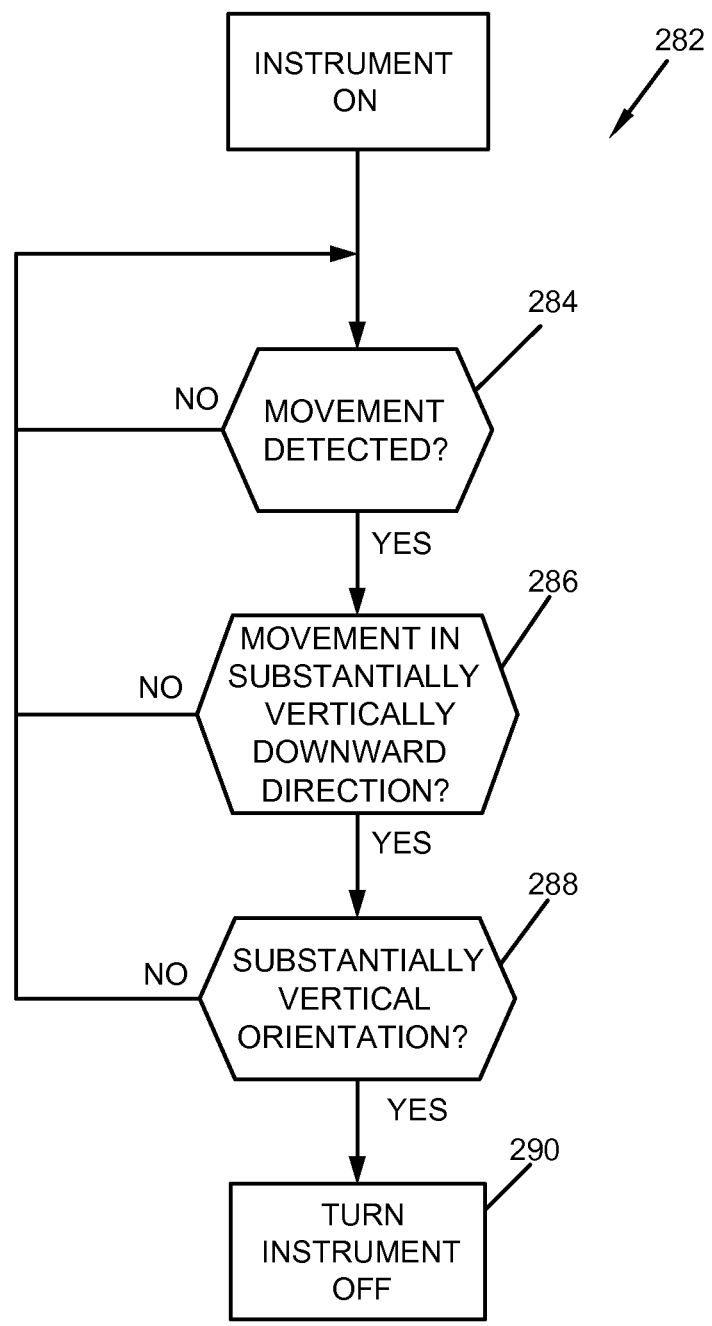
FIG. 13 is a flow chart illustrating an example method of turning OFF an instrument.

FIG. 13 is a flow chart illustrating an example method 282 of turning OFF an instrument 100. In this example, the method 282 includes operations 284, 286, 288, and 290.

The method 282 begins, in this example, when the instrument 100 is turned ON, such as using the method 272, shown in FIG. 10.

The operation 284 is performed to detect movement, such as using the accelerometer 262 shown in FIG. 10.

When movement is detected, operation 286 is performed to determine if the movement detected in operation 284 matches one or more predetermined directions, such as a substantially vertically downward direction. For example, the operation 286 determines whether the movement is in the direction D2, shown in FIG. 11. The predetermined direction is, for example, the direction that the instrument 100 would need to move in order to be returned to the charging cradle 106, when the charging cradle 106 is placed on a horizontal surface, such as a desk or counter top, or mounted to a vertical wall, for example.

Operation 288 is performed to determine if the orientation of the instrument 100 matches one or more predetermined orientations, such as a substantially vertical orientation. The predetermined orientation is, for example, the orientation of the instrument 100 that is required in order to return the instrument 100 to the charging cradle 106, when the charging cradle is placed on a horizontal surface, such as a desk or counter top, or mounted to a vertical wall, for example.

If the results of operations 284, 286, and 288 (which can be performed any desired order) are all "YES," the instrument determines that the instrument 100 is being returned to the cradle, and therefore automatically turns the instrument 100 OFF in operation 290.

Figure 14:
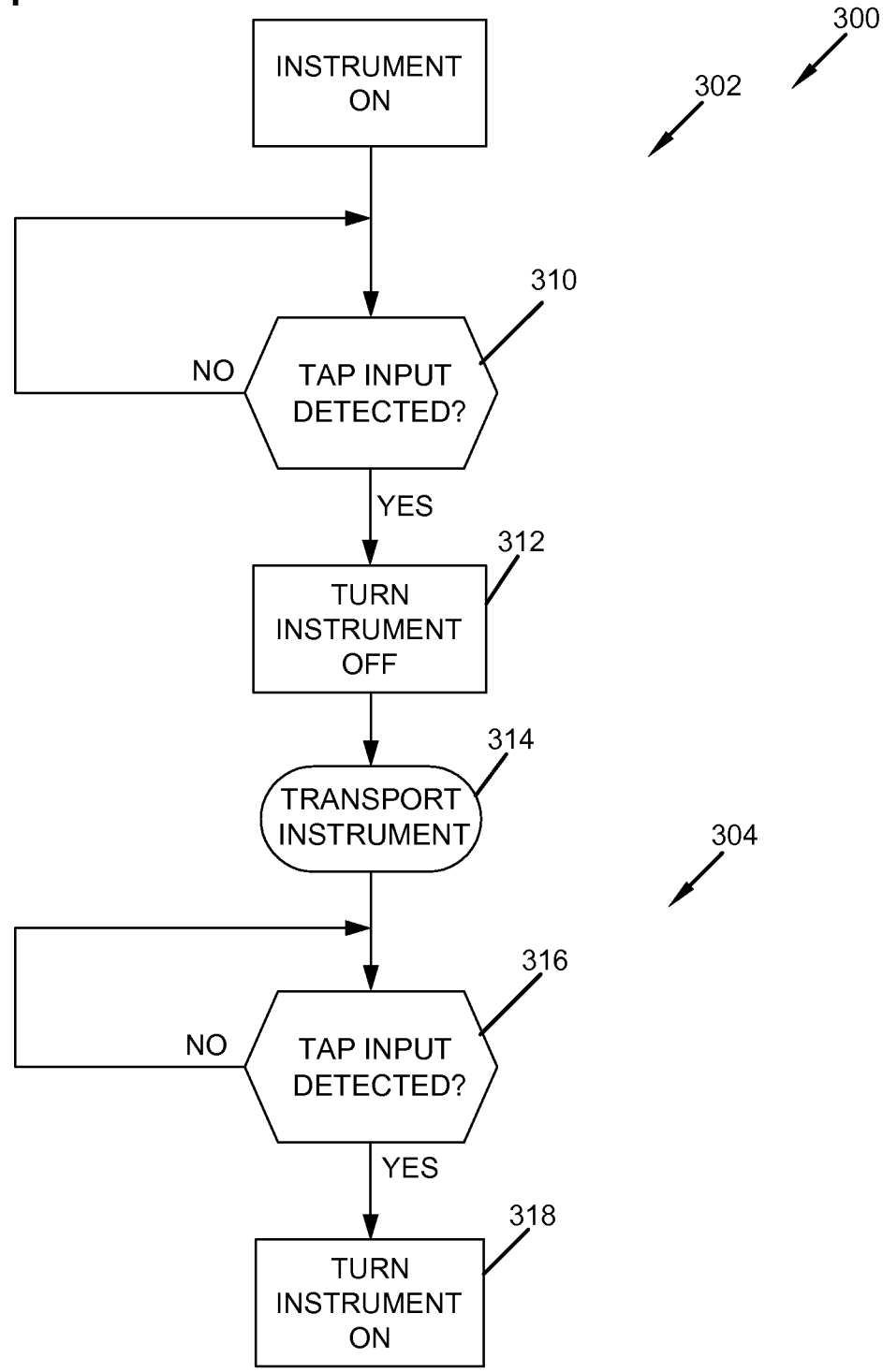
FIG. 14 is a flow chart illustrating a method of operating an instrument in a transportation mode.

FIG. 14 is a flow chart illustrating a method 302 of operating an instrument 100 in a transportation mode. In this example, the method 300 includes a method 302 of temporarily turning OFF an instrument 100, such as to place the instrument 100 into the temporary transportation mode, and also a method 304 of returning the instrument 100 to the normal operating mode. In this example, the method 302 includes operations 310 and 312, and method 304 includes operations 316 and 318.

The method 300 begins with the instrument 100 turned ON. The instrument can be turned on, for example, by removing the instrument from the charging cradle 106, as illustrated in FIG. 12, or using other inputs, as described herein.

The method 302 operates to detect an input from a user indicating that the user wants to place the instrument 100 into a temporary transportation mode. The temporary transportation mode can be used, for example, when the user wants to continue holding the instrument but does not want it to continue operating. For example, the user may want to place the instrument into the user's pocket or set it down somewhere other than in the charging cradle 106, and as a result the user would like the instrument to temporarily turn off.

In this example, the operation 310 is performed to detect a tap input from the user. A tap input is provided by the user by tapping one or more fingers against the housing of the instrument. The tap input is detected using the accelerometer 262, for example.

In some embodiments, a particular combination of taps is required in order for the operation 310 to recognize the movement as a tap input. For example, the tap input may require one, two, three, or more taps. The taps may also be required to occur within a predetermined maximum period of time, but not less than a predetermined minimum period of time.

Upon detection of the tap input, the operation 312 is performed to turn the instrument 100 off. In some embodiments, the instrument is placed into a lower power sleep mode. In other embodiments, the instrument is placed into a lower power transportation mode, in which tap input detection continues to be active, in order to perform operation 316.

Once the instrument 100 has been turned off, the instrument 100 can then be transported, set down, or otherwise handled in operation 314.

The operation 316 is then performed to detect a tap input. The tap input can be the same or a different tap input as detected in operation 310.

Upon detection of the tap input in operation 316, the instrument 100 is turned on 318 to resume normal operation.

Figure 15:
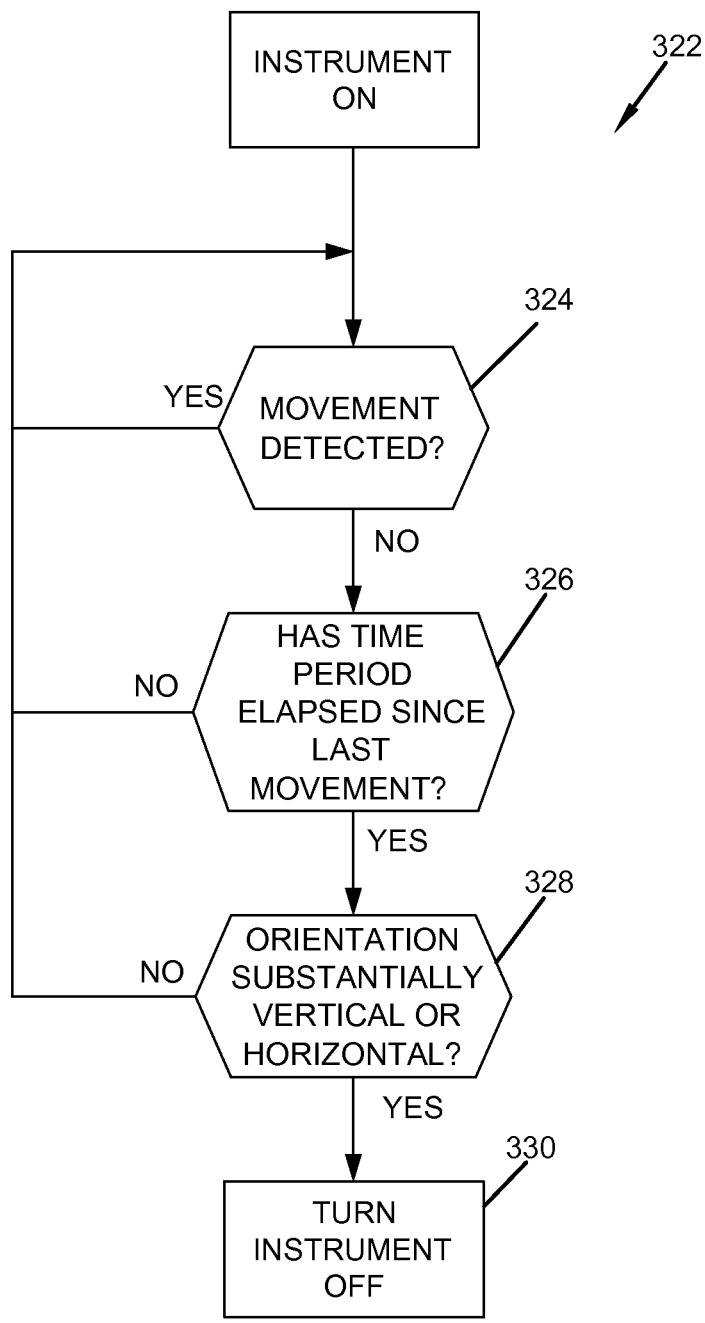
FIG. 15 is a flow chart illustrating a method of automatically turning OFF an instrument when the instrument is not in use.

FIG. 15 is a flow chart illustrating a method 322 of automatically turning OFF an instrument 100 when the instrument is not in use. In this example, the method includes operations 324, 326, 328, and 330.

The method begins with the instrument 100 ON. The instrument can be turned on by using any one of the techniques described herein.

The operation 324 is performed to detect movement of the instrument 100. If movement is detected, the instrument 100 is determined to be currently in use. Accordingly, the method 322 repeats the operation 324 until no movement is detected.

Once no movement is detected, the operation 326 is performed to determine whether a predetermined time period has elapsed since the last detected movement of the instrument 100. The operation 326 waits until the predetermined period of time has elapsed. In some embodiments, operation 330 is then performed to turn off the instrument.

In another possible embodiment, however, the operation 328 is performed to determine the orientation of the instrument 100. If the orientation of the instrument 100 is substantially aligned with one or more predetermined orientations, then the instrument 100 is turned off 330. As an example, the predetermined orientations may be the orientation of the instrument 100 when it is placed on a flat surface (i.e., horizontal) or when it is placed in the charging cradle 106 (i.e., vertical).

A benefit of operation 328 is that it can help prevent the instrument 100 from turning off when the instrument is being held very still during use. So long as the instrument 100 is not oriented as it would be if it were set down on a flat surface, the instrument 100 continues to remain ON.

Once the device is determined to not be currently in use (upon detection of no movement, for a sufficient period of time, and optionally by being oriented substantially in a given orientation), the operation 330 is performed to turn off the instrument 100.

Figure 16:
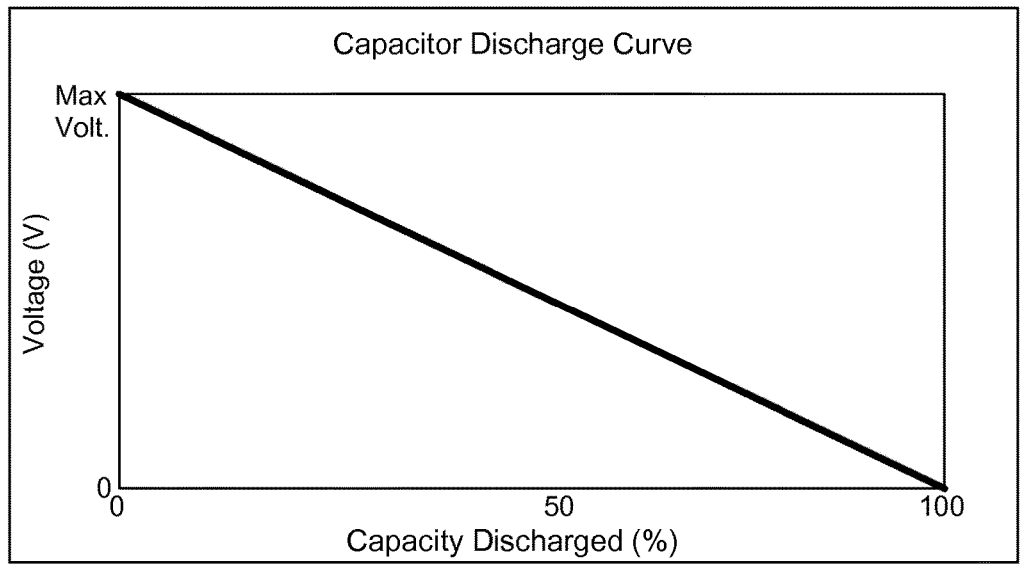
FIG. 16 illustrates a discharge curve of a capacitor.

FIG. 16 is a schematic diagram illustrating an exemplary discharge curve for an example capacitor 124. As shown in FIG. 16, the output voltage from the capacitor 124 is directly proportional to the amount (%) of energy that has been discharged from the capacitor. When the capacitor is fully charged, the capacitor's output voltage is at a maximum. The voltage decreases proportionally as the energy is depleted, until no energy remains in the capacitor.

Figure 17:
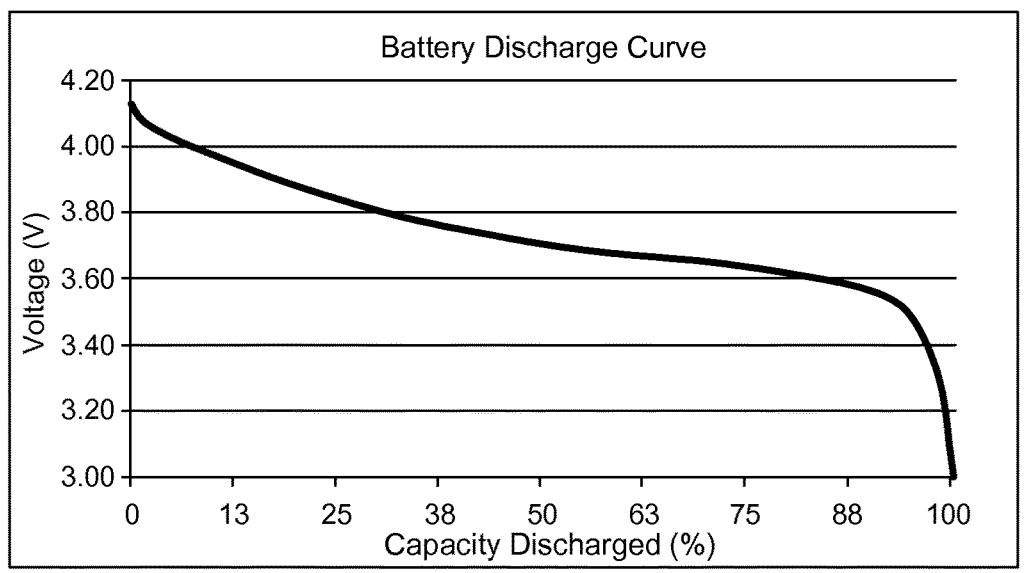
FIG. 17 illustrates a discharge curve of a battery, and the modified discharge curve provided by a mimic circuit shown in FIG. 18.

In contrast, FIG. 17 is a schematic diagram illustrating an exemplary discharge curve of an example lithium ion battery. The output voltage decreases much more gradually, varying only between about 3.5V and 4.1 volts across most of the discharge curve. When the battery is nearly depleted (e.g., around 90% discharged), the voltage decreases more rapidly.

Many electronic devices are designed to operate with batteries, which supplies a much more constant output voltage. Such electronic devices may not work if a capacitor were substituted in place of the battery, because the capacitor may not have a suitable voltage level to begin with, and even if an adequate voltage can be initially provided, the output voltage will decrease too rapidly.

If, instead, a boost circuit is provided, such as described herein, a substantially constant output voltage can be provided. However, a constant output voltage can also be undesirable. For example, if the electronic device includes a battery charge status indicator, such a device may rely upon and require that the power source provide the expected discharge curve. If it doesn't, the charge status indicator may simply show that the battery is fully charged until the power source is depleted.

Figure 18:
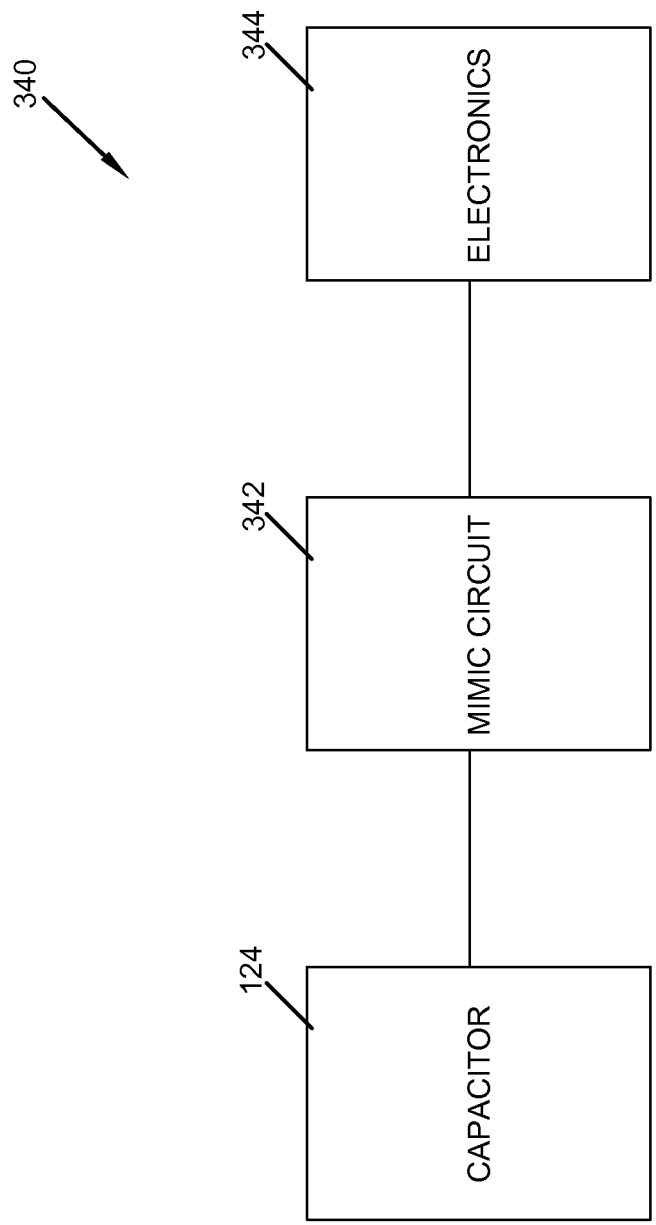
FIG. 18 is a schematic block diagram illustrating a mimic circuit interfacing between a capacitor and electronics.

FIG. 18 is a schematic block diagram illustrating a mimic circuit 342 interfacing between a capacitor 124 and electronics 344. In some embodiments, the mimic circuit 342 transforms the output from the capacitor 124 into an output suitable for the electronics 344, such as to mimic the discharge curve of one or more batteries. This permits the capacitor 124 and mimic circuit 342 to replace one or more batteries for powering the electronics 344, without requiring any changes to the electronics 344. In other words, electronics 344 that are designed to be powered by batteries, can instead by powered by one or more capacitors 124 without modifying electronics 344.

The capacitor 124 can be one or more capacitors. Other power sources may also be used in other embodiments, such as a battery, a solar cell, or other power supply circuit.

The electronics 344 can be any electronic device. In some embodiments the electronic device is at least part of a handheld instrument, such as the instrument 100 described herein. Typically the electronics 344 are designed to be powered by a certain power source, such as a battery. However the mimic circuit 342 permits the electronics to instead by powered by a different power source, such as the capacitor 124, having a different output and/or discharge characteristic.

Figure 19:
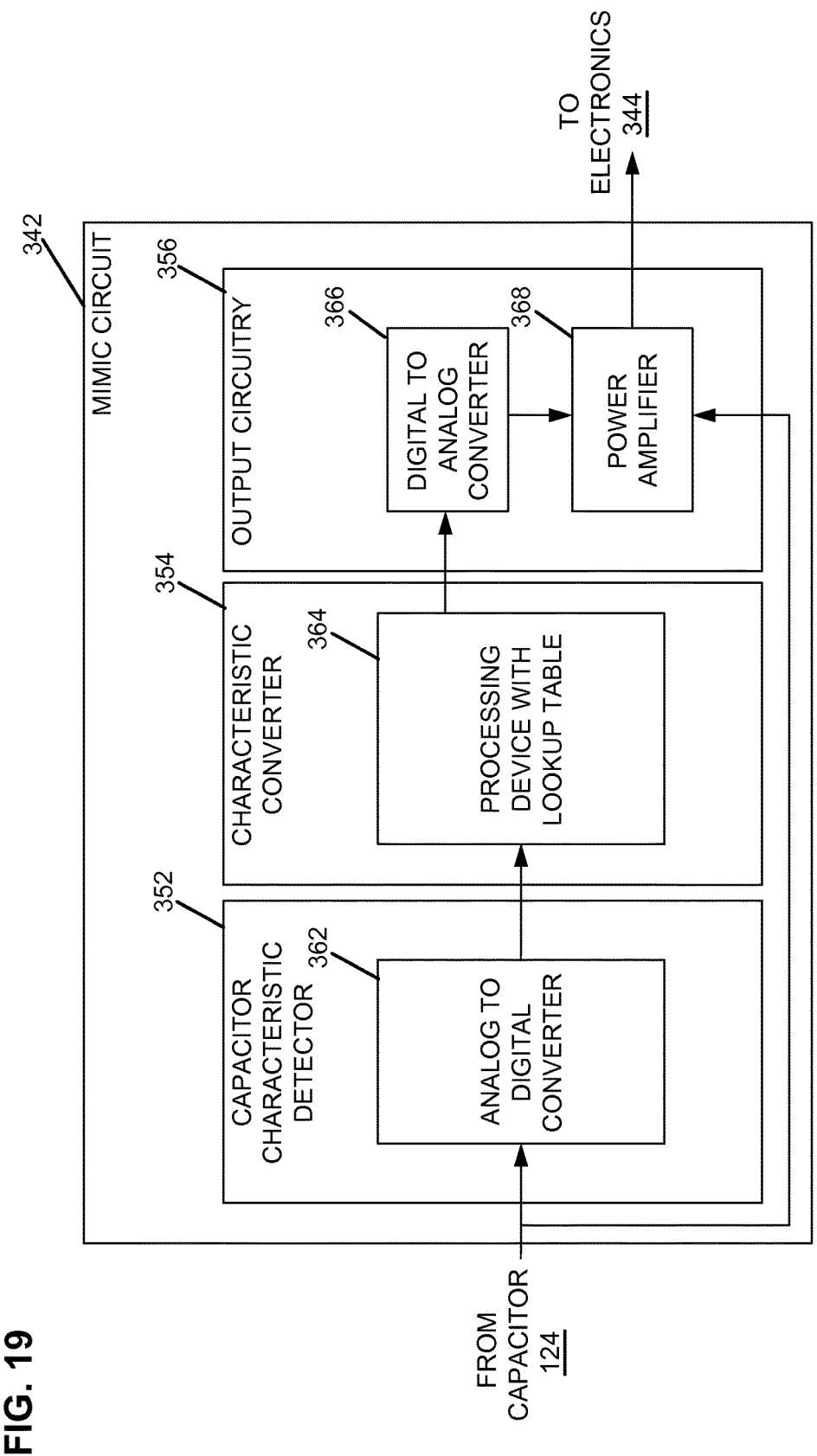
FIG. 19 is a schematic block diagram illustrating an example packaging of a capacitor and mimic circuit.

FIG. 19 is a schematic block diagram illustrating an example of the mimic circuit 342. In this example, the mimic circuit includes a capacitor characteristic detector 352, a characteristic converter 354, and output circuitry 356.

The capacitor characteristic detector 352 is electrically connected to and evaluates one or more characteristics of the capacitor 124. One example of a characteristic of a capacitor is the voltage across the capacitor 124. Another example of a characteristic of a capacitor is the amount of energy that has been discharged from the capacitor. Either characteristic can be used to mathematically compute the other characteristic. In other embodiments, different characteristics can be determined by the capacitor characteristic detector.

One example of the capacitor characteristic detector 352 is an analog to digital converter. The analog to digital converter can be a part of a processing device (e.g., 196, shown in FIG. 5), part of the boost converter (e.g., 192, shown in FIG. 4) or a separate device.

As one example, the capacitor characteristic detector 352 detects a voltage provided by the capacitor, which may follow the capacitor discharge curve illustrated in FIG. 16.

The characteristic converter 354 operates to convert the capacitor characteristic detected by the capacitor characteristic detector 352, and convert that characteristic into a desired characteristic. One example of a desired characteristic is a voltage of a battery, according to a predetermined battery discharge curve.

One example of the characteristic converter 354 is a processing device (e.g., 196, shown in FIG. 5) which stores a lookup table encoding the predetermined battery discharge curve, such as the exemplary discharge curve illustrated in FIG. 17.

Because different power sources have different discharge curves, the characteristic converter can be configured to provide any desired discharge curve. Even different batteries have different discharge curves. Therefore, in some embodiments the discharge curve is selected to match the discharge curve of a battery for which the electronics 344 are designed to operate. Examples of batteries having various different discharge curves include lithium ion, Nickel-metal hydride, alkaline, and a variety of other batteries. The outputs of other non-battery power sources can alternatively be matched in yet other embodiments.

The output circuitry 356 generates the desired output characteristic determined by the characteristic converter 354. For example, the output circuitry 356 converts the output voltage from the capacitor 124 into a different output voltage, where the output voltage is the voltage that would be provided by a battery with the same percentage of discharge.

As one example, the output circuitry 356 includes a digital to analog converter 366 and a power amplifier. The output circuitry 356 receives an 8-bit digital input from the processing device 364, representing the appropriate output voltage. The digital to analog converter 366 generates the desired output voltage. The power amplifier 368 then amplifies the output, such as to provide an adequate current to drive the electronics 344 at the output voltage.

Figure 20:
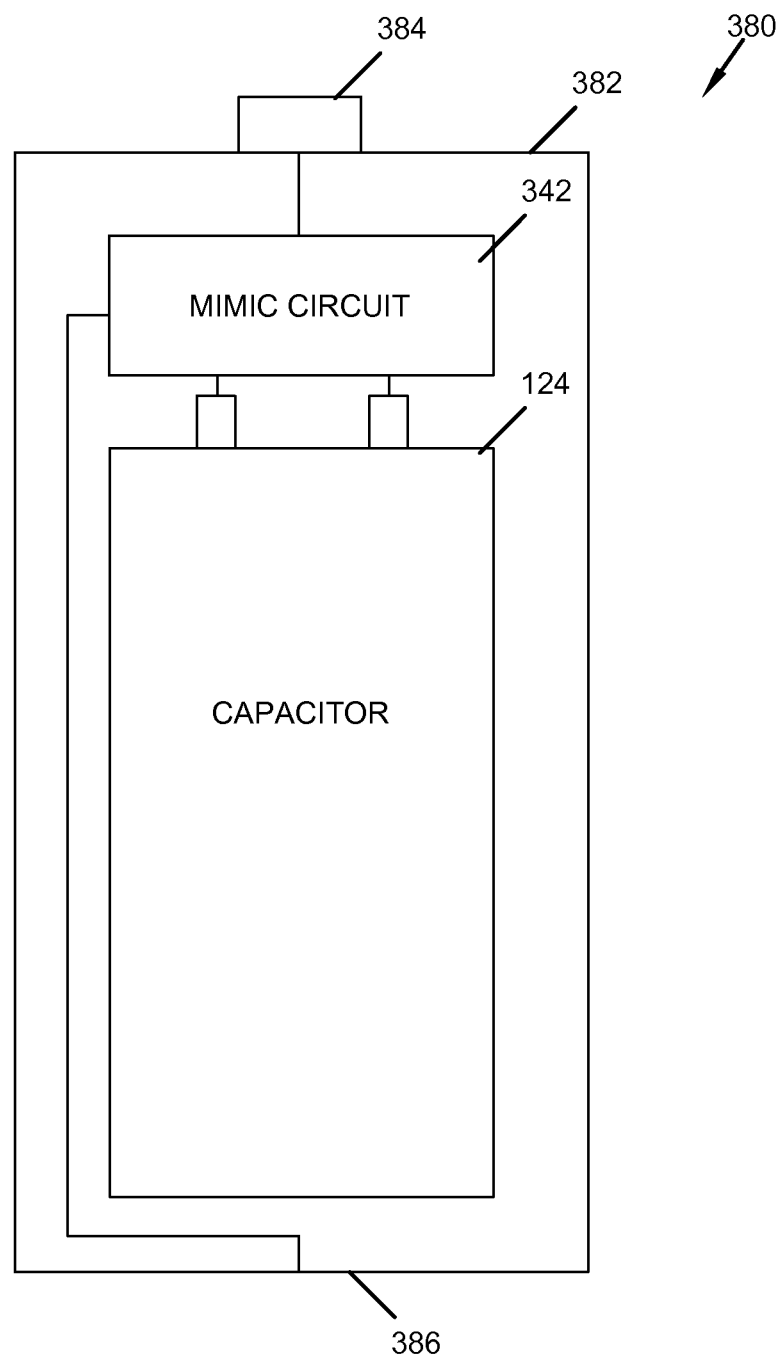
FIG. 20 is a schematic block diagram illustrating an example of the mimic circuit shown in FIG. 19.

FIG. 20 illustrates an exemplary battery replacement device 380. In this example, the battery replacement device 380 includes a capacitor 124, a mimic circuit 342, and a packaging 382. The packaging 382 includes a positive terminal 384 and a negative terminal 386.

The battery replacement device 380 includes a packaging 382 that is arranged and configured to replace a battery in an electronic device. Accordingly, the packaging 382 is sized and shaped to fit within a battery compartment of the electronic device, and may have a size and shape that is the same as a corresponding battery, or a combination of multiple batteries (such as two or more batteries arranged in series or parallel). In particular, in some embodiments the battery replacement device 380 has a positive terminal 384 positioned at the same location as the positive terminal of the corresponding battery, and a negative terminal 386 positioned at the same location as the negative terminal of the corresponding battery (or batteries).

The capacitor 124 is arranged within the packaging 382 and is electrically connected to the mimic circuit 342. Electrical conductors connect the mimic circuit and/or the capacitor 124 to the appropriate terminals 384 and 386.

In some embodiments, the packaging 382 is sized and shaped like a battery, such as any of the following batteries: AAA, AA, C, D, 4.5-Volt, 9-Volt, Lantern, watch or coin style batteries, or any other desired battery configuration.

Figure 21:
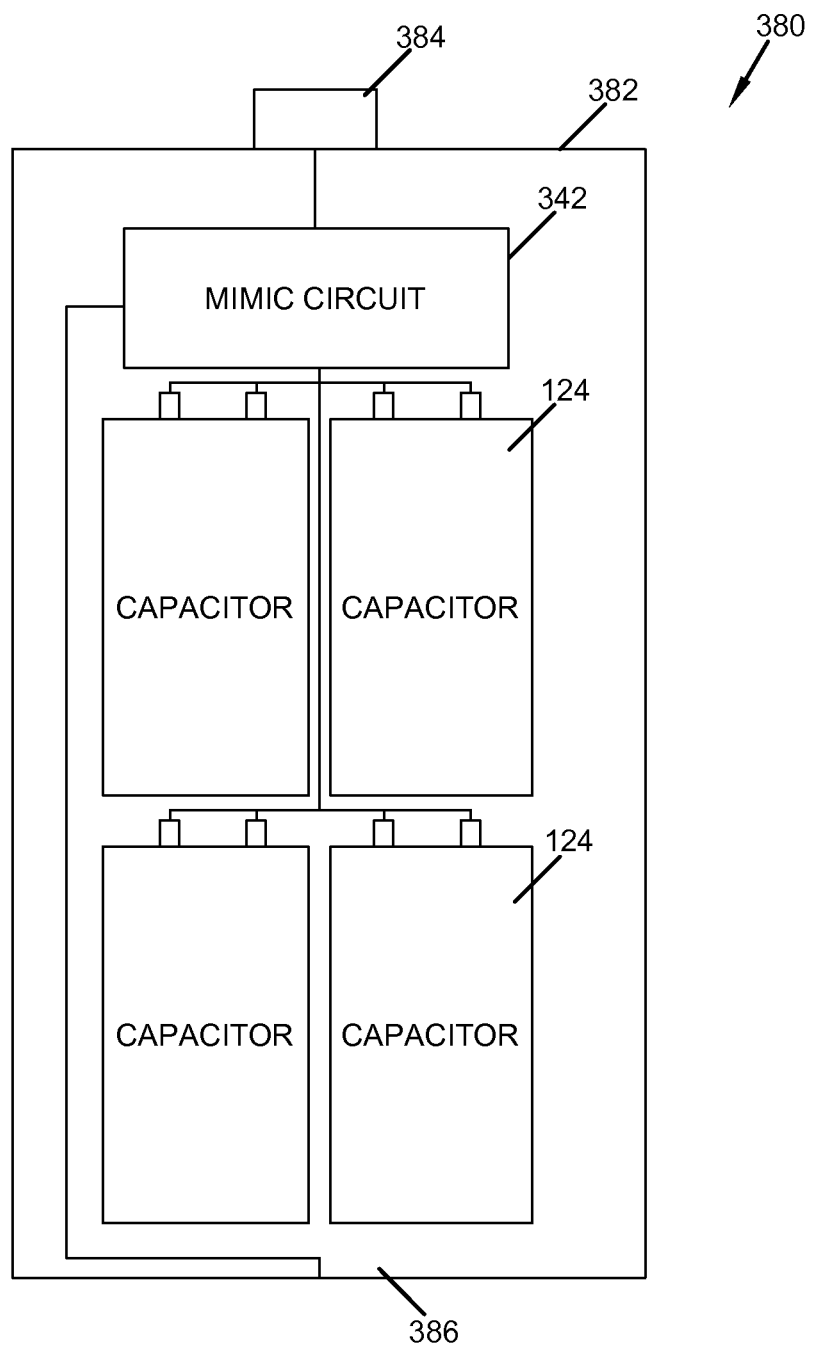
FIG. 21 is a schematic block diagram illustrating another example packaging of multiple capacitors and a mimic circuit.

FIG. 21 illustrates another exemplary battery replacement device 390, showing that the battery replacement device can include multiple capacitors 124. As with the example shown in FIG. 20, the battery replacement device 390 includes one or more mimic circuits 342 and packaging 382. The capacitors 124 can be connected in series or in parallel, or in any combination thereof.

Additionally it should be noted that multiple battery replacement devices can be used in some embodiments, such as being arranged in series or in parallel. For example, the positive terminal of a first battery replacement device can be connected to a negative terminal of a second battery replacement device and inserted into an electronic device in place of two (or more) series-connected batteries.

Figure 22:
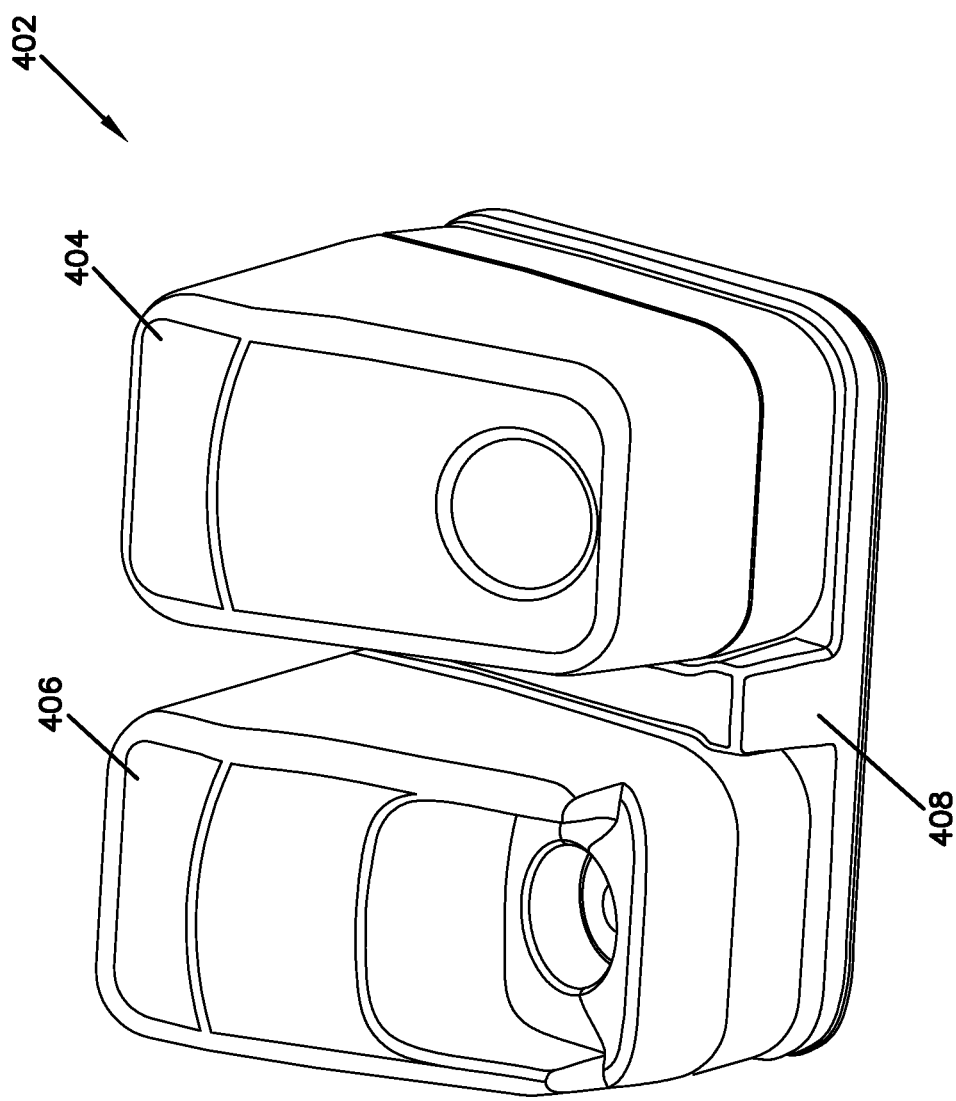
FIG. 22 is a perspective view of an example dual charging station.
Figure 23:
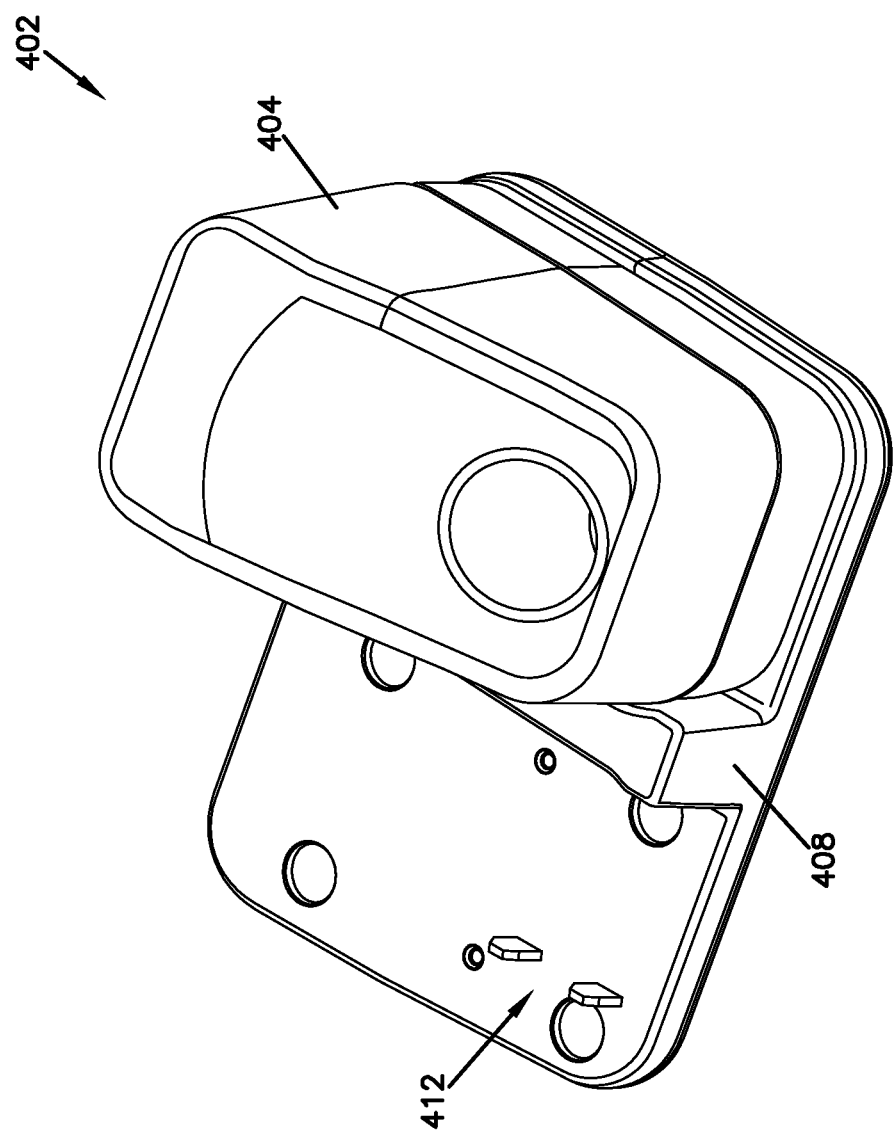
FIG. 23 is another perspective view of the example dual charging station with one of the charging stations being removed.
Figure 24:
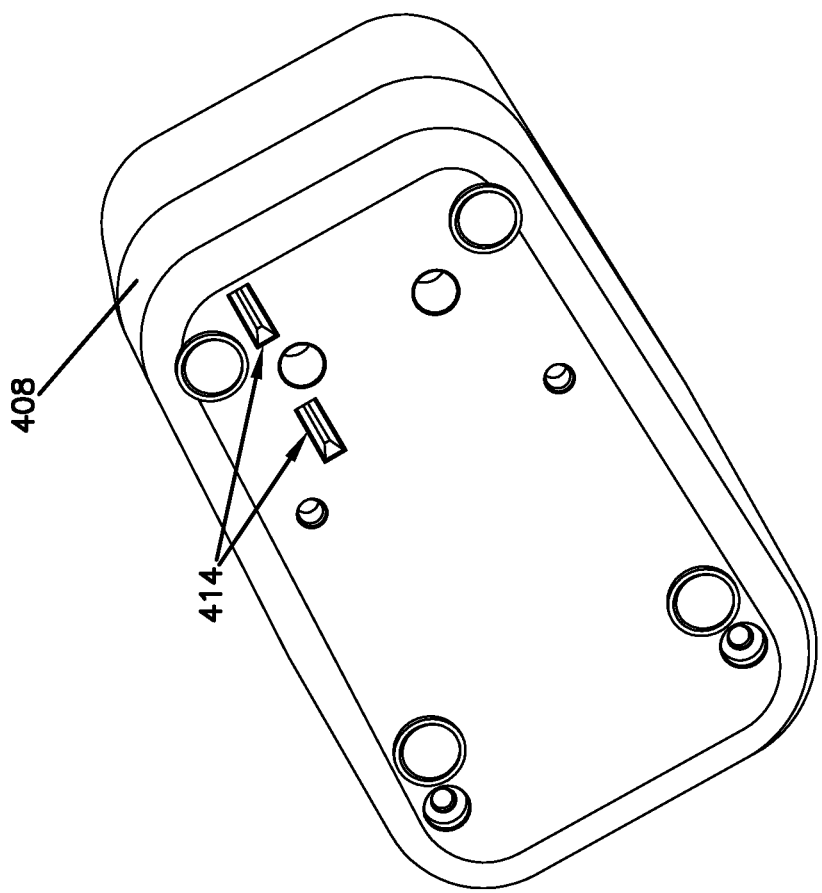
FIG. 24 is a perspective view of a base of the charging station that is removed in FIG. 23.

FIGS. 22-24 illustrate an example dual charging station 402. It is sometimes desirable to electrically power multiple charging stations 402 from a single power source. For example, it is sometimes desirable to reduce the number of power cords. By charging multiple stations from a single power source (with a single power cord), additional power cords are not required.

FIG. 22 is a perspective view of an example dual charging station 402. In this example, the dual charging station 402 includes a master station 404, a slave station 406, and a base 408.

The master station 404 is a charging cradle, such as the example charging cradle 106 illustrated and described with reference to FIG. 1. In some embodiments, the master charging station 404 includes a power cord through which power can be received from a wall receptacle.

The slave station 406 is also a charging cradle. In this example, the slave station 406 does not include a power cord, and instead obtains power from the master station 404 through the base 408.

In another possible embodiment, the base 408 can have its own power cord for receiving power from a wall receptacle. The stations 404 and 406 are both powered by the base 408.

The example shown in FIG. 22 illustrates stations 404 and 406 having differently sized and/or shaped receptacles. Accordingly, in some embodiments the stations 404 and 406 are configured for charging different instruments 100. For example, station 404 has a receptacle having a round cross-sectional shape, while the station 406 has a receptacle having a square cross-sectional shape. In another possible embodiment, however, both stations 404 and 406 can have the same type of receptacle, such as for charging multiple instruments 100 at once.

Some embodiments include more than two stations, such as three or four stations. Other devices may also be powered by connection or coupling with one or more of the stations 404 and 406, or the base 408 in some embodiments.

FIG. 23 is another perspective view of the example dual charging station 402 with one of the charging stations 406 removed to reveal features of the base 408.

Specifically, the base includes a connector 412. The connector 412 is configured to make an electrical connection between the base 408 and the slave station 406. A similar connector is provided on the other side of the base 408 for connection with the master station 404.

One or more electrical conductors are arranged in the base to conduct electricity between the master station 404 connector and the slave station 406 connector 412. In this way the slave station 406 can be powered by the master station 404.

FIG. 24 is a bottom perspective view of the slave station 406. The slave station includes one or more ports 414 configured to receive pins from connector 412, shown in FIG. 23, to permit the slave station 406 to receive power provided by the master station 404 through the base 408.

ADDITIONAL EMBODIMENTS

Additional embodiments include the following, or any combination thereof, or combinations thereof:

A device comprising a mimic circuit, for battery VI curves, derived from a super capacitor to facilitate a drop in, one for one, battery replacement in a device, wherein the mimic circuit fits into the same space as a traditional battery volume including the super capacitor as well.

A device wherein the device has a charge time of less than one minute.

A device further comprising a motion sensing feature, wherein the sensing feature can determine when the device is being transported.

A device further comprising a motion sensing feature, wherein the sensing feature can determine when the device is being used.

A device further comprising sense output feature to detect the difference between Halogen and LED bulbs and adjust VI curves accordingly.

A device wherein the super capacitors can be made to different shapes that conform to product shapes.

A device further comprising a 360 degree visual indicator ring of indicating status of the remaining energy within the handle by changing colors and flashing and/or combinations.

A device further comprising a 360 degree visual indicator ring of indicating status of the remaining energy within the handle by changing colors and flashing and/or combinations.

A device further comprising a user interface that takes advantage of the accelerometer to anticipate how the device is being used or stored or moved.

A device wherein the super capacitors yield ability to build sealed devices that never require service and further enable improved cleaning because of the sealing.

A device wherein single or multiple cells may be stacked in series or in parallel for increased energy storage.

A device wherein super capacitors can be charged either while the device is physically on the patient or not.

A device further comprising a battery free handle backwards compatible with 3.5 v devices.

A device wherein the super capacitors can be configured in a portable power pack mode.

A device wherein a device using super capacitors can be charged using either AC power supplies or from any USB compliant device.

A device wherein the super capacitors can be used in either digital or non digital devices.

A device wherein the device is selected from the group comprising vaginal speculum illuminators, laryngoscopes, temperature testing devices, ECG devices, BP devices, SPO2 devices, SPOT monitors, otoscopes, episcopes, opthalmoscopes, digital imaging devices, hearing testing equipment, or headlights.

A device further comprising a means to improve super capacitor life by cycle charging caps at the end of their charge cycle.

A device further comprising a means to boost the extremely low voltage directly off the super capacitor to a usable circuit voltage therefore utilizing more of the available total energy stored.

A device further comprising an energy gauging method that enables precise understanding of total energy stored or total energy available.

A device further comprising a simplified constant current charger that enables super fast charging.

A device wherein the super capacitor temporarily stores energy quickly within a device or even between devices using other super capacitors.

A device wherein the capacitor can be hot swapped.

A device wherein the super capacitors enable devices that derive their power from various forms of energy harvesting as a means to store energy quickly and safely.

A device wherein the device can be used in emergency medicine as devices requiring quick recharge are now made possible.

A charging station comprising: a module architecture configurable as single or duals or modular to adapt to future shapes while still using the same charging techniques.

A device comprising: a super capacitor; and a dimming feature.

A device wherein the dimming feature comprises an accelerometer and capsense combination.

A device further comprising a 360 degree touch surface for control of the intensity of the handle using capsense.

A device further comprising a user interface enabling multiple functions out of a single touch such as sensing more than one finger and alternating variables after each touch and sensing multiple fingers.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A battery replacement device comprising:
    a packaging including at least a positive terminal and a negative terminal, the packing having a size and shape of at least one battery;
    at least one capacitor disposed in the packaging; and
    a mimic circuit electrically coupled to receive power from the at least one capacitor and deliver the power to at least one of the positive and negative terminals, wherein the mimic circuit changes an output characteristic of the at least one capacitor into an output characteristic of the battery, the mimic circuit comprising:
        a capacitor characteristic detector that evaluates a first characteristic of the at least one capacitor, comprising an analog to digital converter that detects an output voltage from the at least one capacitor;
        a characteristic converter that converts the first characteristic into a second different characteristic, the characteristic converter comprising a processing device that utilizes a lookup table to determine the second different characteristic based on the first characteristic of the at least one capacitor; and
        output circuitry configured to generate the second different characteristic from the first characteristic, wherein the output circuitry further comprises:
            a digital to analog converter that receives a digital signal from the processing device and generates an output voltage; and
            a power amplifier that generates an amplified output at the output voltage to power an electronic device.

2. The battery replacement device of claim 1, wherein the output characteristic is a discharge characteristic.

3. The battery replacement device of claim 2, wherein the discharge characteristic is an output voltage associated with a percentage of a capacity of the capacitor that has been discharged.

4. The battery replacement device of claim 1, wherein the at least one capacitor is one or more super capacitors.

5. The battery replacement device of claim 1, wherein the packaging has the size and shape of one of: AAA, AA, C, or D type battery.

* * * * *